United States Patent
Hong et al.

(10) Patent No.: US 8,530,687 B2
(45) Date of Patent: Sep. 10, 2013

(54) CATALYSTS, METHODS OF MAKING CATALYSTS, AND METHODS OF USE

(75) Inventors: Sukwon Hong, Gainesville, FL (US); Hwimin Seo, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 210 days.

(21) Appl. No.: 13/225,952

(22) Filed: Sep. 6, 2011

(65) Prior Publication Data

US 2012/0059182 A1    Mar. 8, 2012

Related U.S. Application Data

(60) Provisional application No. 61/380,359, filed on Sep. 7, 2010.

(51) Int. Cl.
| | | |
|---|---|---|
| C07F 1/12 | (2006.01) | |
| C07F 13/00 | (2006.01) | |
| C07F 15/00 | (2006.01) | |
| B01J 31/00 | (2006.01) | |

(52) U.S. Cl.
USPC ............ 556/112; 502/152; 556/46; 556/136; 556/140

(58) Field of Classification Search
USPC .................... 556/46, 112, 136, 140; 502/152
See application file for complete search history.

(56) References Cited

U.S. PATENT DOCUMENTS

| | | | |
|---|---|---|---|
| 6,103,937 A | 8/2000 | Baker et al. | |
| 6,911,546 B2 | 6/2005 | Hedrick et al. | |
| 7,053,221 B2 | 5/2006 | Hedrick et al. | |
| 7,071,218 B2 | 7/2006 | Pfahl et al. | |
| 2010/0041895 A1 | 2/2010 | Robinson et al. | |
| 2010/0044688 A1 | 2/2010 | Wolleb et al. | |
| 2011/0114922 A1 | 5/2011 | Pretot et al. | |
| 2011/0118475 A1 | 5/2011 | Thadani et al. | |

FOREIGN PATENT DOCUMENTS

WO    2010003226 A1    5/2011

OTHER PUBLICATIONS

Wanniarachchi et al., Organometallics, vol. 27, No. 1, pp. 21-24 (2008).*

Kremzow et al., Chem, Eur. J., vol. 11, pp. 1833-1853 (2005).*

Legrande M. Slaughter, "Covalent Self-Assembly of Acyclic Diaminocarbene Ligands at Metal Centers", Comments on Inorganic Chemistry, vol. 29, Issue 1&2, Jan. 2008, pp. 46-72.

Wolfgang A. Herrmann, et al., "Metal complexes of acyclic diaminocarbenes: links between N-heterocyclic carbene (NHC)- and Fischer-carbene complexes", Journal of Organometallic Chemistry, vol. 684, Issue 1-2, Nov. 1, 2003, pp. 235-248.

Evelyn L. Rosen, et al., "Synthesis and Study of the First N-Aryl Acyclic Diaminocarbene and Its Transition-Metal Complexes", Organometallics, Issue 26 (24), 2007, pp. 5774-5777.

(Continued)

Primary Examiner — Porfirio Nazario Gonzalez

(74) Attorney, Agent, or Firm — Thomas Horstemeyer, LLP

(57) ABSTRACT

Embodiments of the present disclosure provide for acyclic diaminocarbenes (ADCs) catalysts such as those shown in FIG. 1.1 and in the Examples, methods of making catalysts, methods of using catalysts, and the like. Catalyst of the present disclosure can be useful in various catalytic transformations. Embodiments of the catalyst can be used in hydroamination, cycloisomerization, allylic rearrangement reactions, alkyne hydration reactions, Meyer-Schuster rearrangement reactions, and the like.

15 Claims, 19 Drawing Sheets

Compound A

Compound B

Compound C

(56) References Cited

OTHER PUBLICATIONS

Mary S. Collins, et al., "Differentially Substituted Acyclic Diaminocarbene Ligands Display Conformation-Dependent Donicities", Organometallics, Issue 29, 2010, pp. 3047-3053, DOI:10.1021/om1004226.

David R. Snead, et al., "Bis(2-alkylpyrrodlidin-1-yl)methylidenes as Chiral Acyclic Diaminocarbene Ligands" Organometallics, Issue 29 (7), 2010, pp. 1729-1739.

Evelyn L. Rosen, et al., "Olefin Metathesis Catalysts Containing Acyclic Diaminocarbenes", Organometallics, Issue 29 (1), 2010, pp. 250-256, DOI: 10.1021/om9008718.

Joan Vignolle, et al. "Stable Noncyclic Singlet Carbenes", Chemical Reviews, Issue 109 (8), 2009, pp. 3333-3384.

David R. Snead, et al., "A New Route to Acyclic Diaminocarbenes via Lithium-Halogen Exchange", Organic Letters Issue 11 (15), 2009, pp. 3274-3277, DOI: 10.1021/ol9013156.

Javier Ruiz, et al., "Acyclic Diamino Carbene Complexes of Manganese(I): Synthesis, Deprotonation, and Subsequent Multiple Insertion Reaction of Alkynes", Organometallics, Issue 28 3), 2009, pp. 830-836, DOI: 10.1021/om80088r.

Natalie Fey, et al., "A ligand knowledge base for carbenes (LKB-C): maps of ligand space", Dalton Transactions, 2009, pp. 8183-8196, DOI: 10.1039/B909229C.

Dimitri Hirsch-Weil, et al. "In situ generation of novel acyclic diaminocarbene-copper complex", Chemical Communications, 2009, pp. 2475-2477, DOI: 1039/B821169H.

* cited by examiner

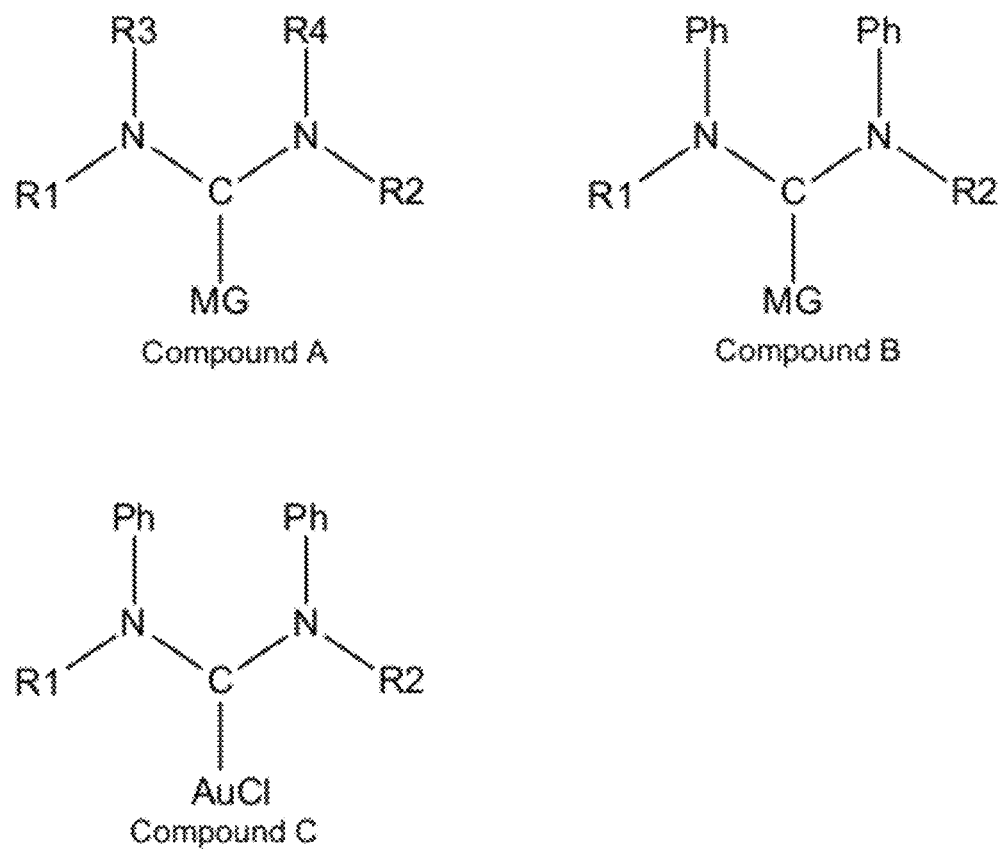
FIG. 1.1

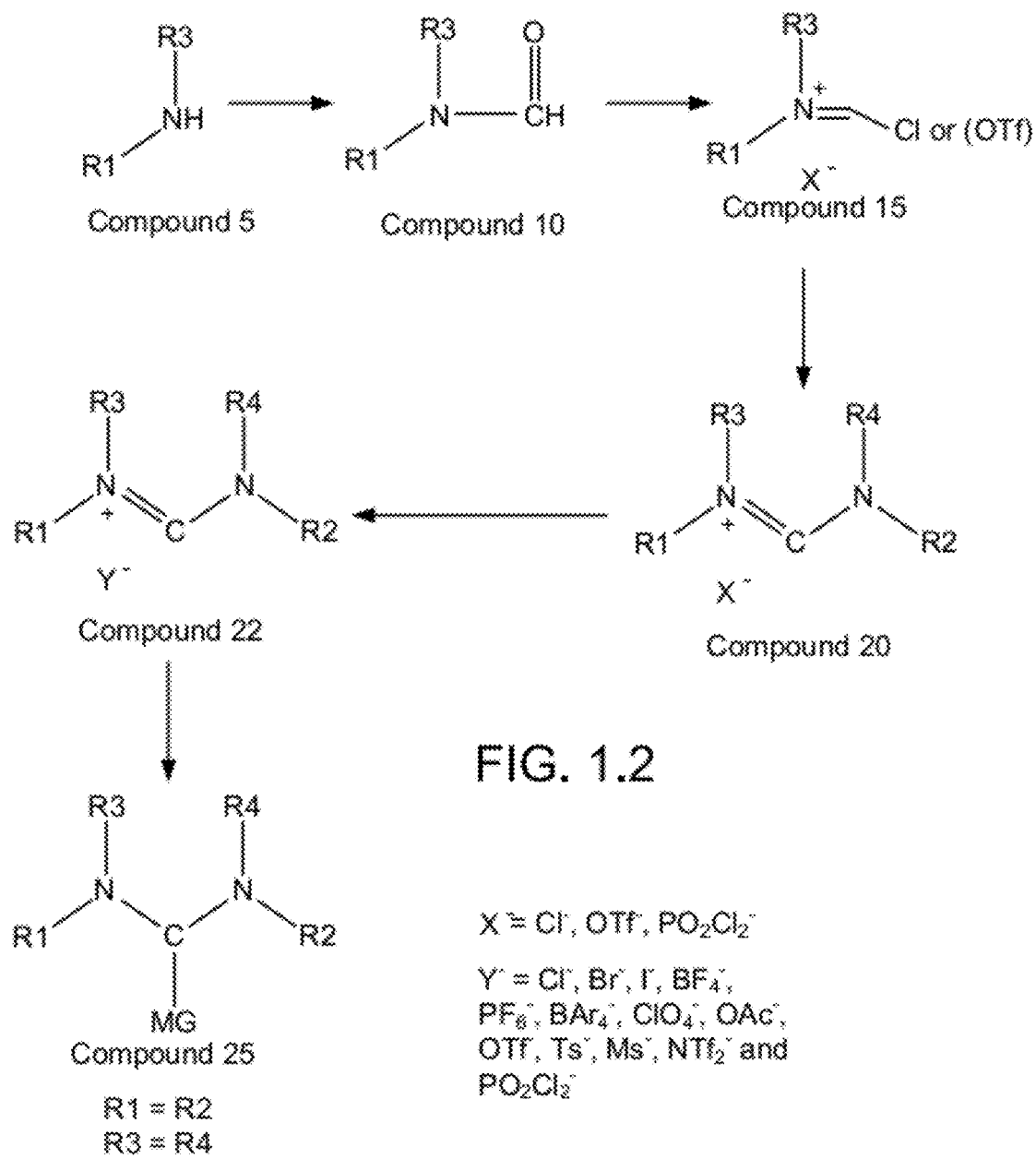
FIG. 1.2

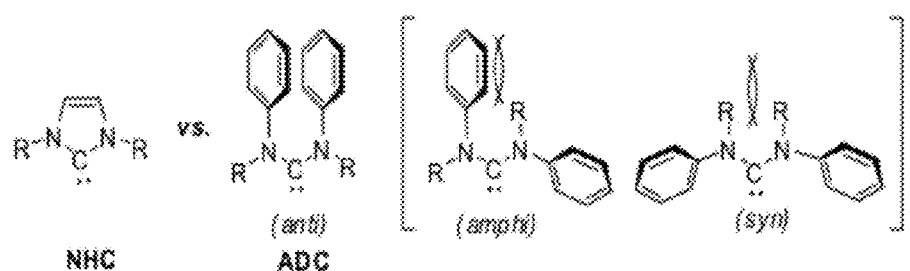
FIG. 2.1
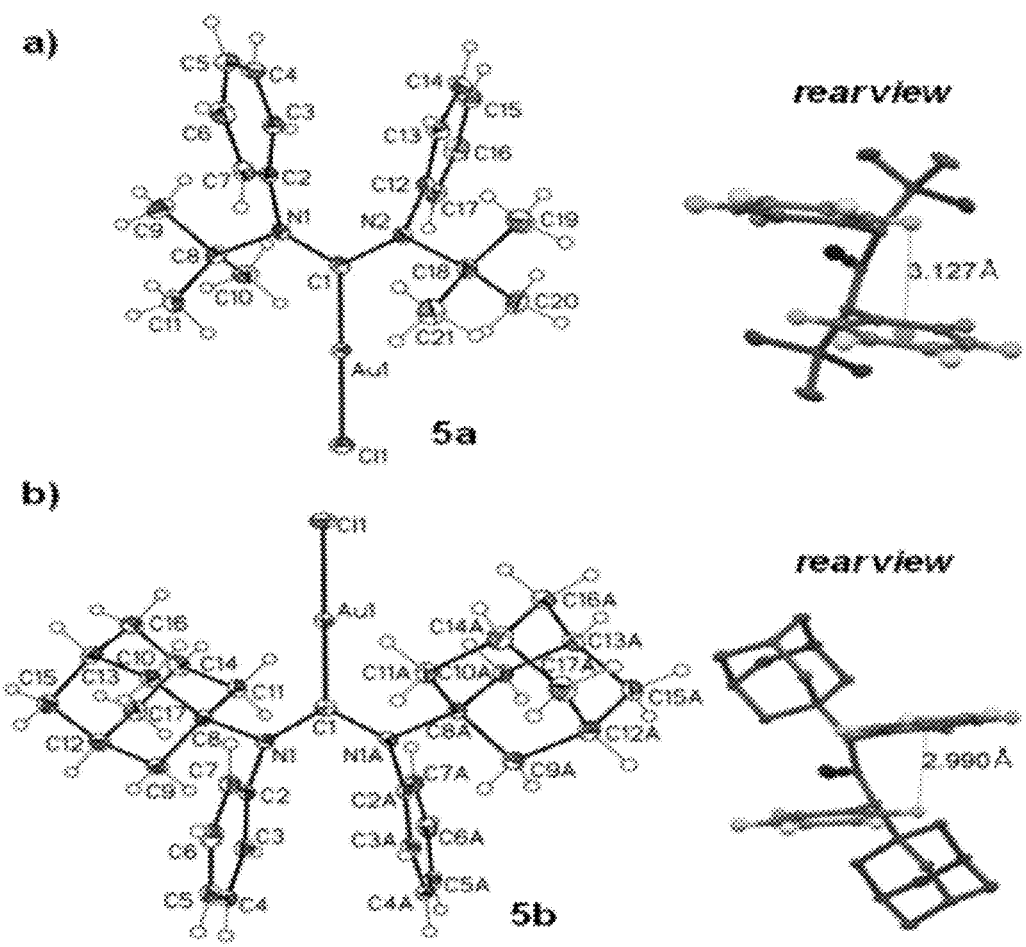
FIG. 2.2

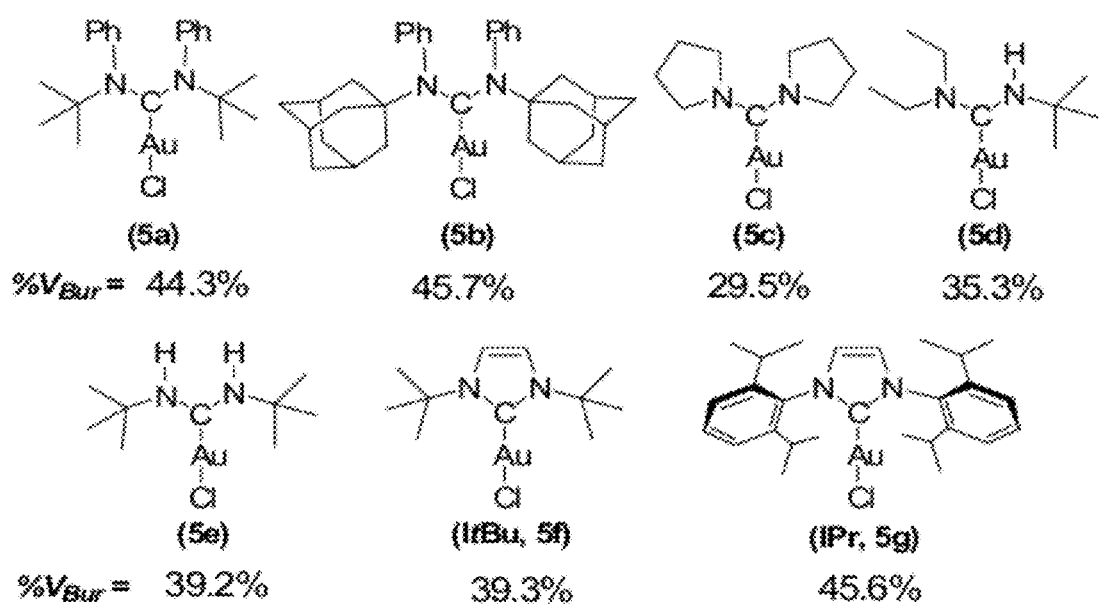
FIG. 2.3

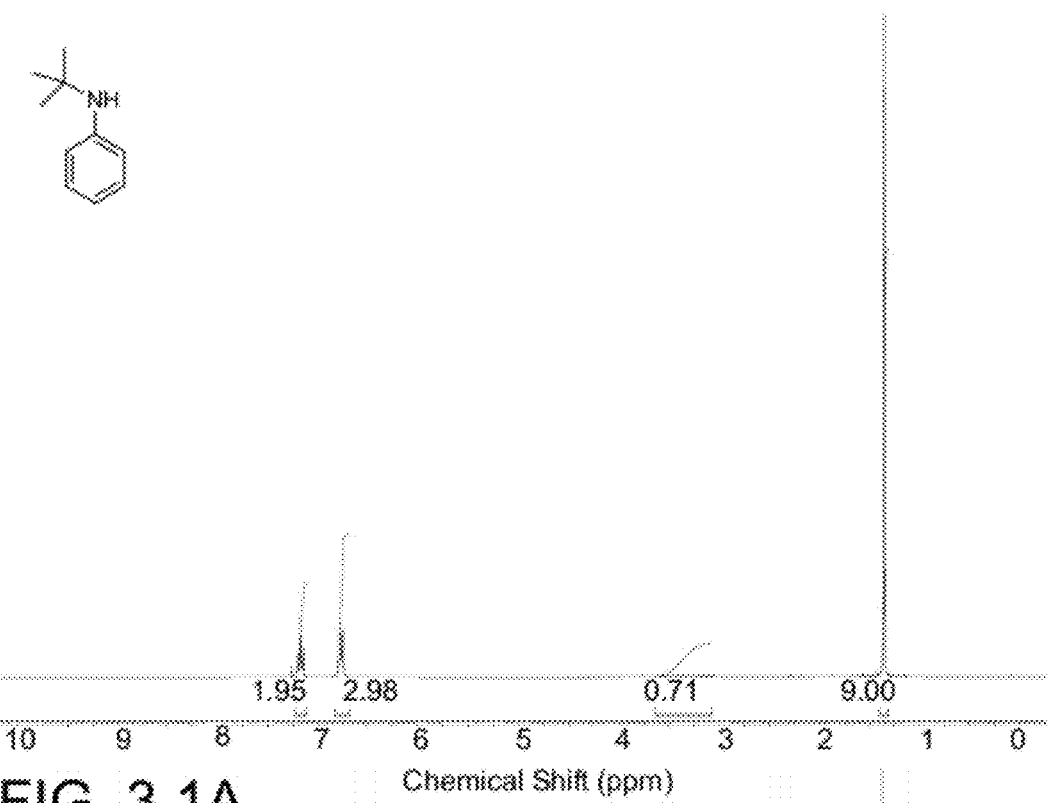
FIG. 3.1A
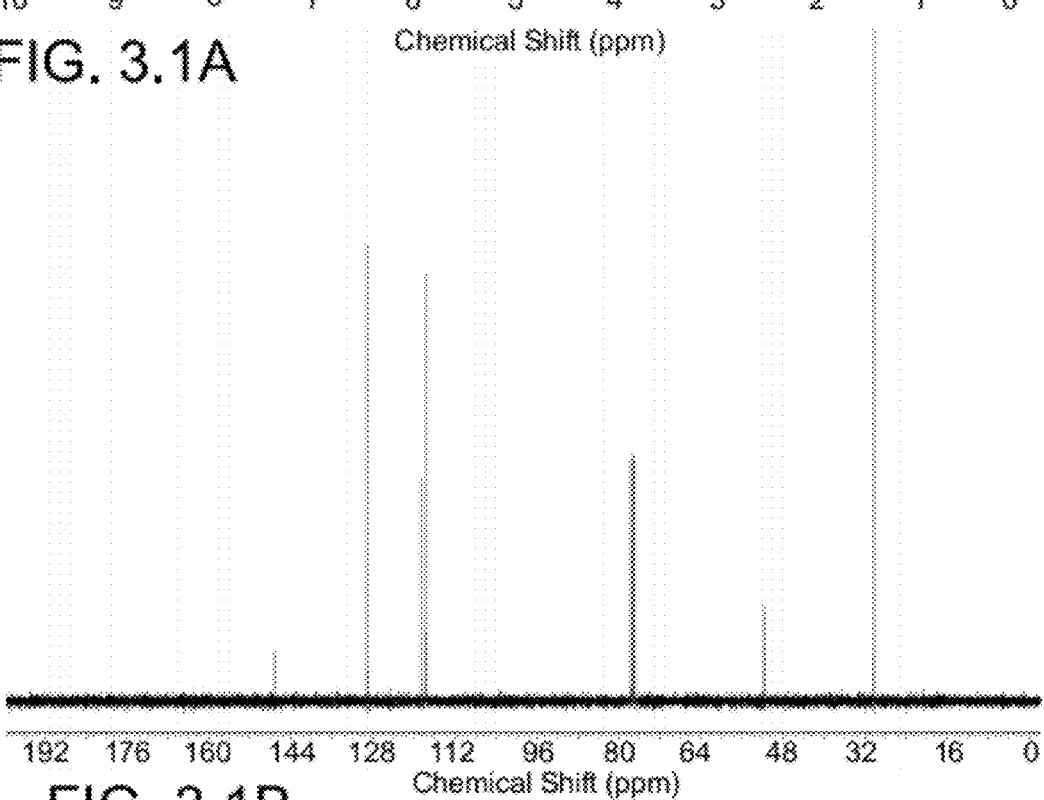
FIG. 3.1B

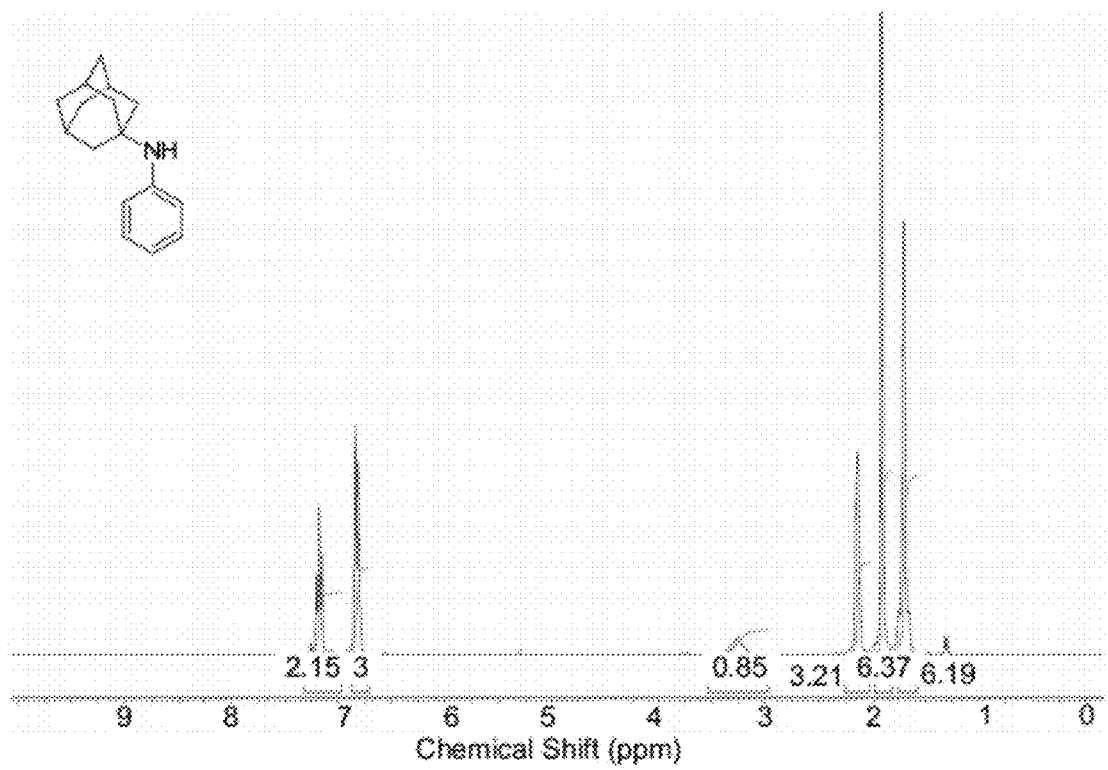
FIG. 3.1C

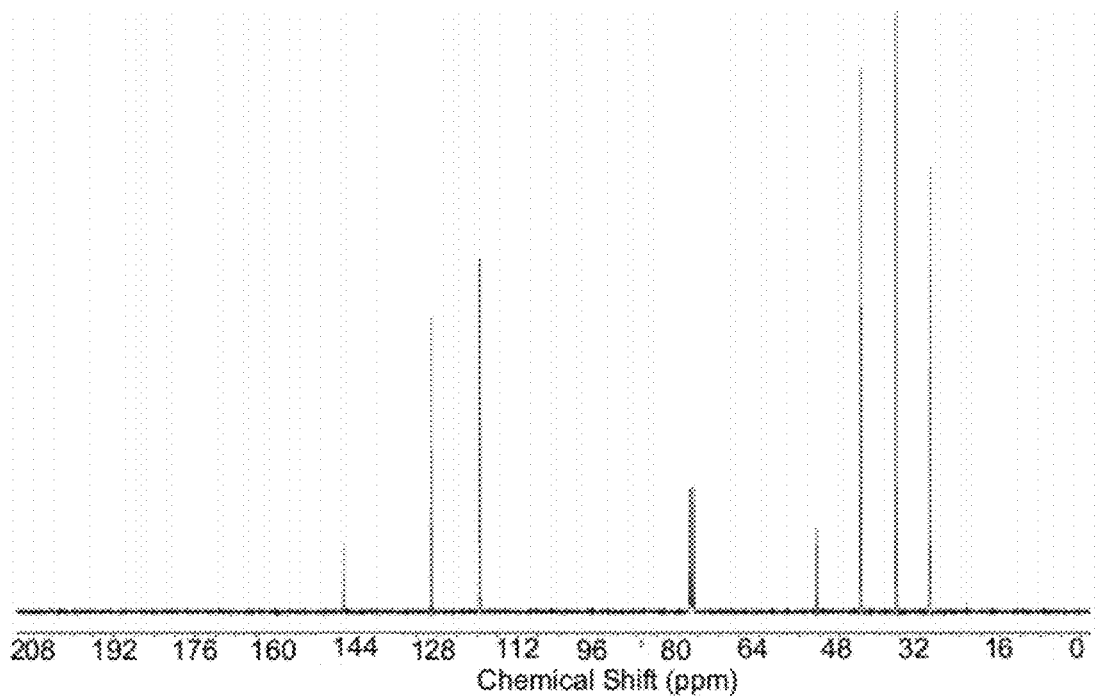
FIG. 3.1D
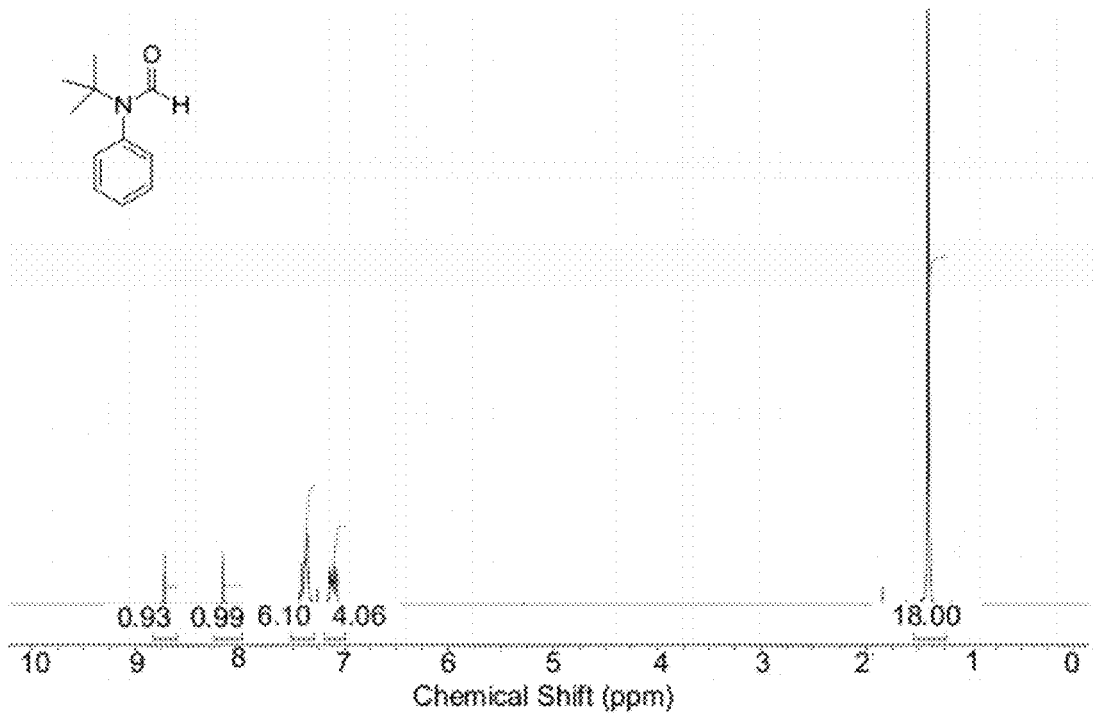
FIG. 3.1E

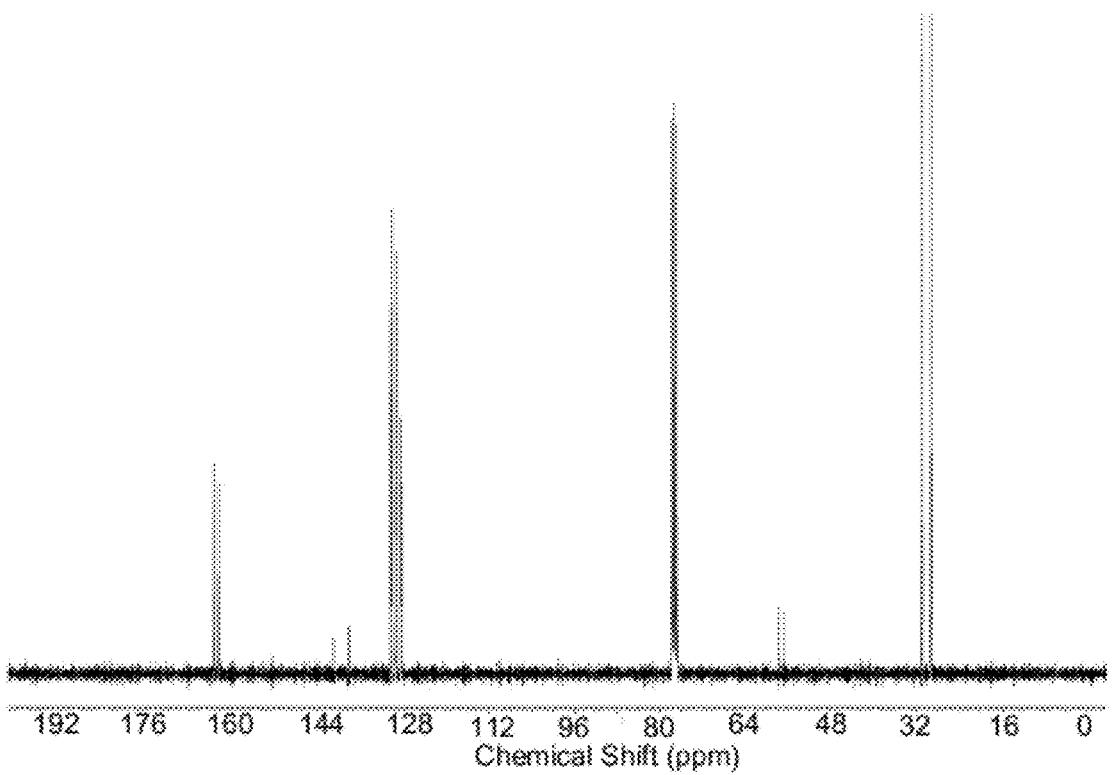
FIG. 3.1F
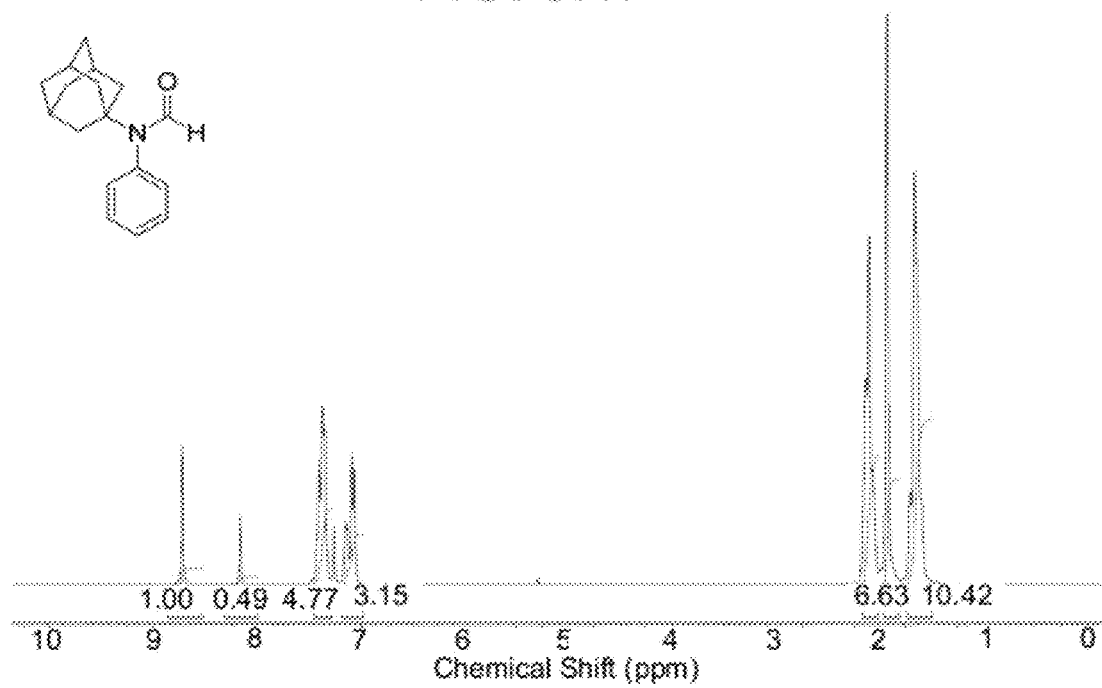
FIG. 3.G

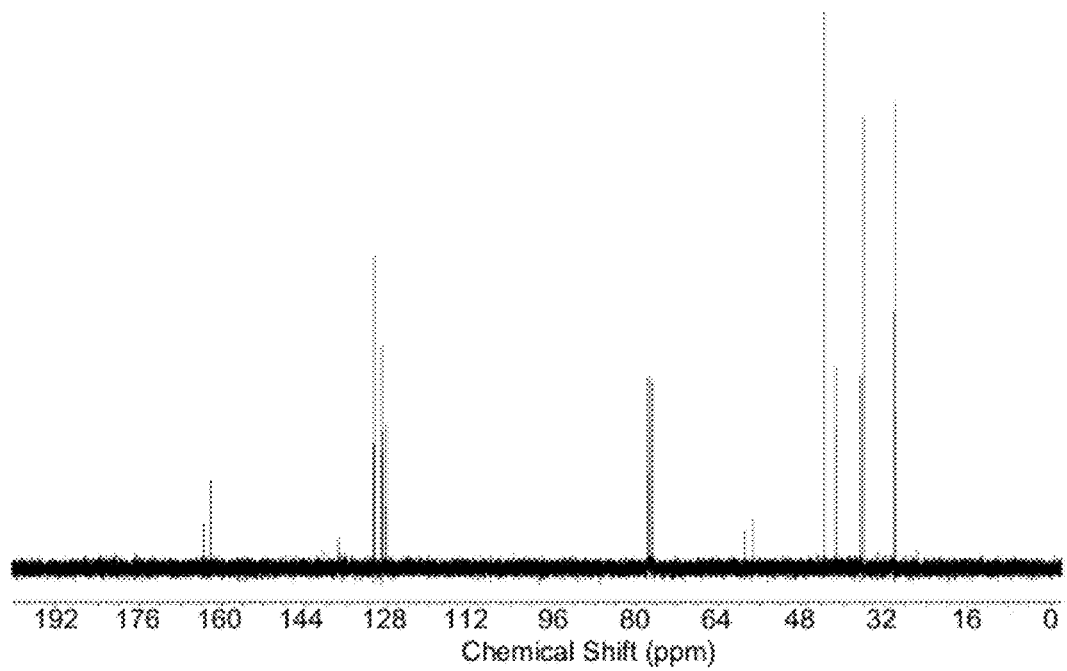
FIG. 3.1H
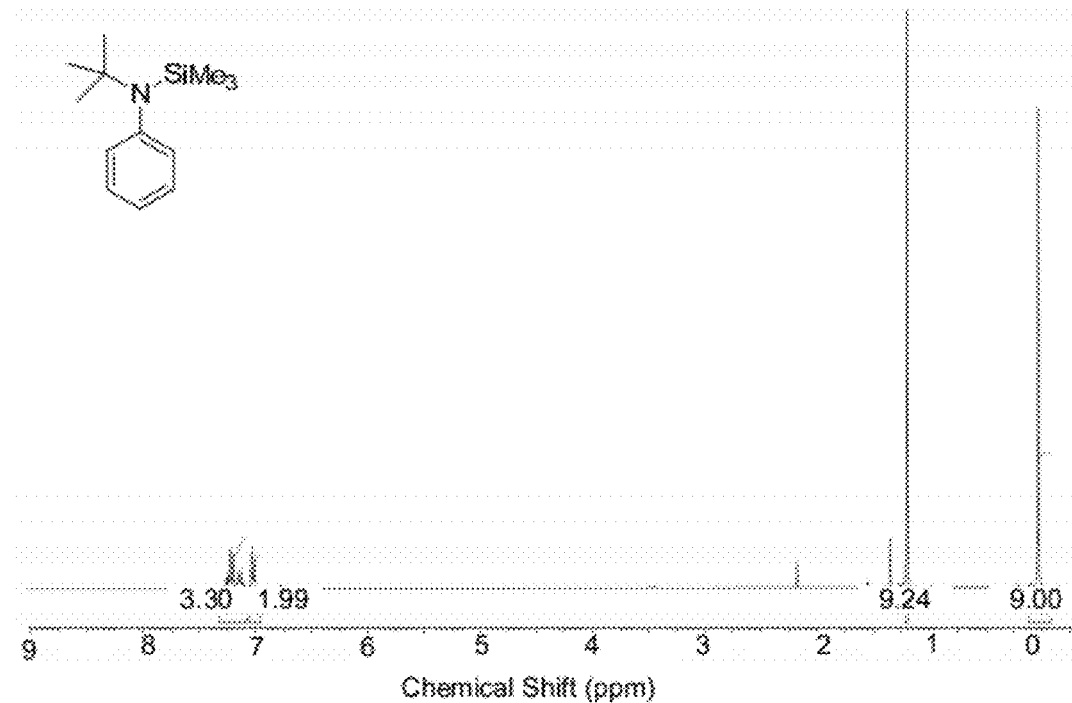
FIG. 3.1I

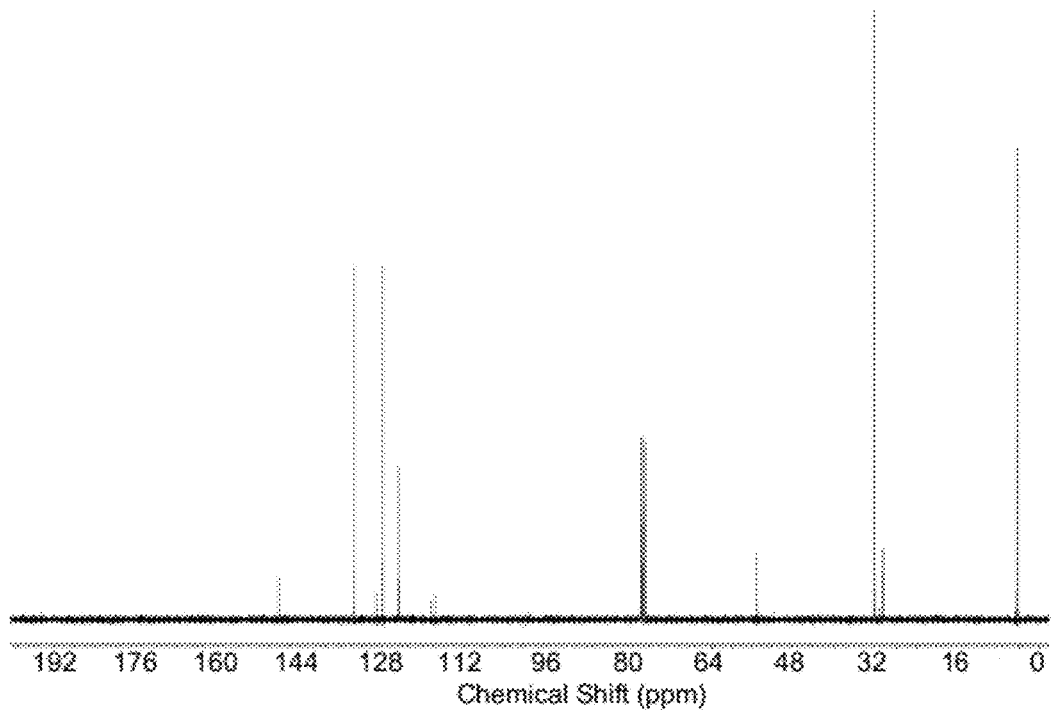
FIG. 3.1J
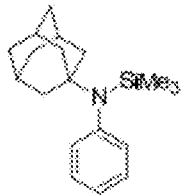
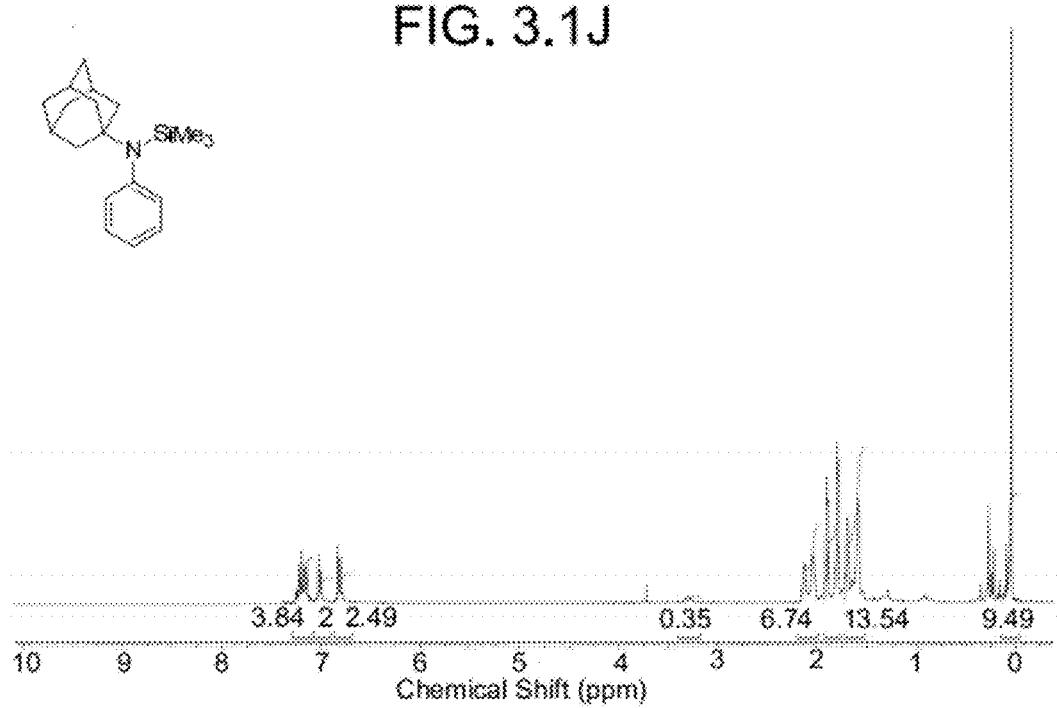
FIG. 3.1K

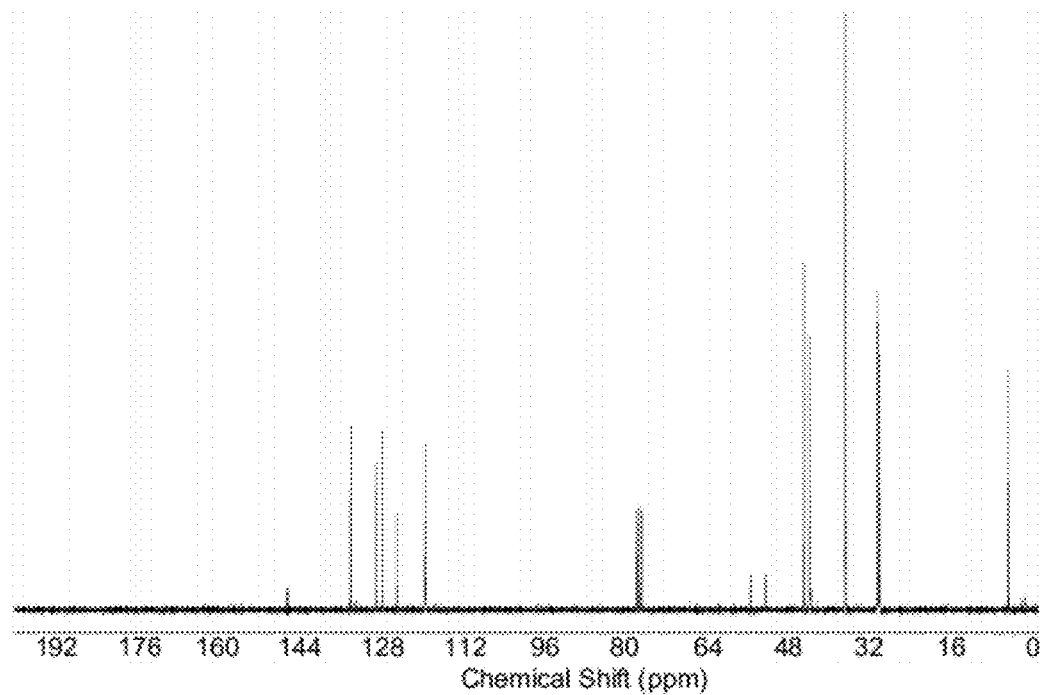
FIG. 3.1L
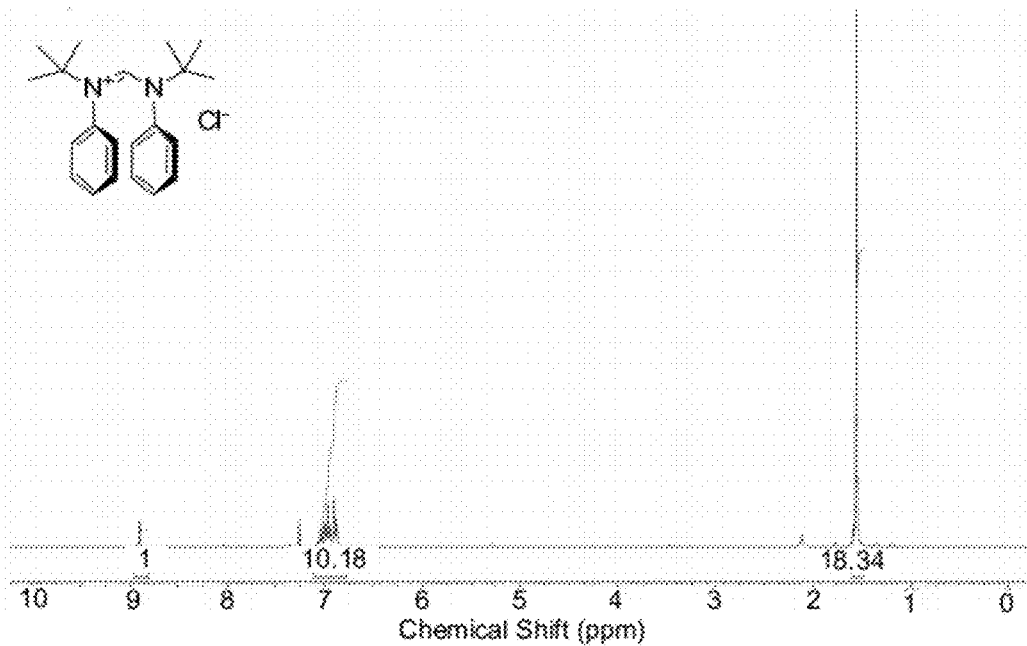
FIG. 3.1M

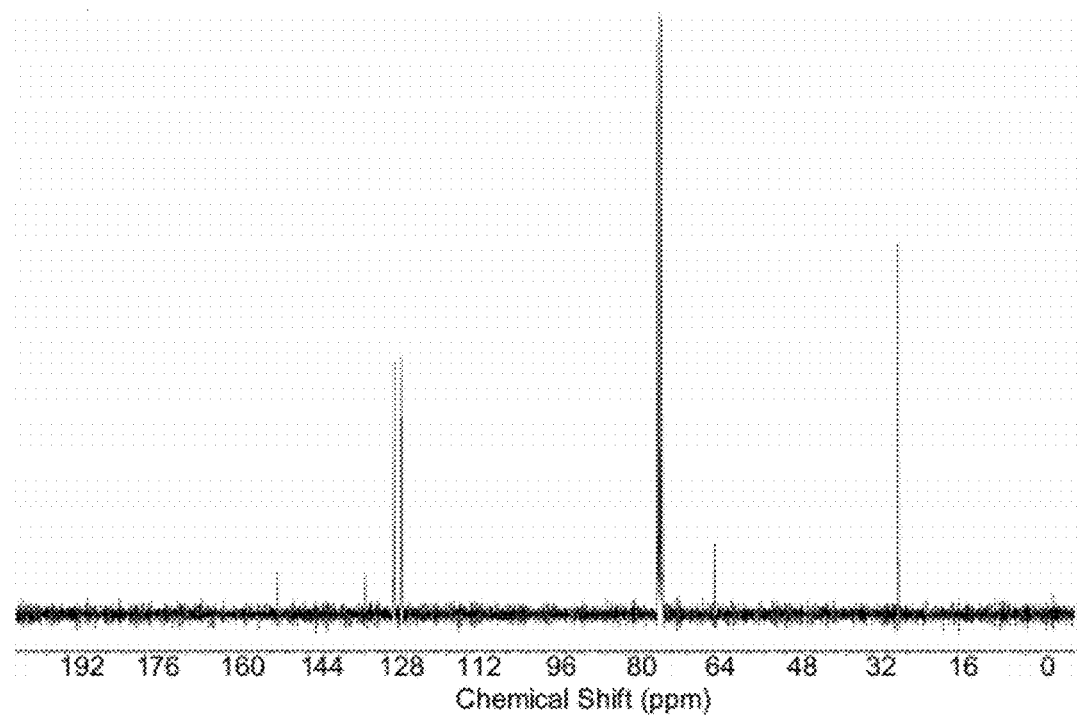
FIG. 3.1N
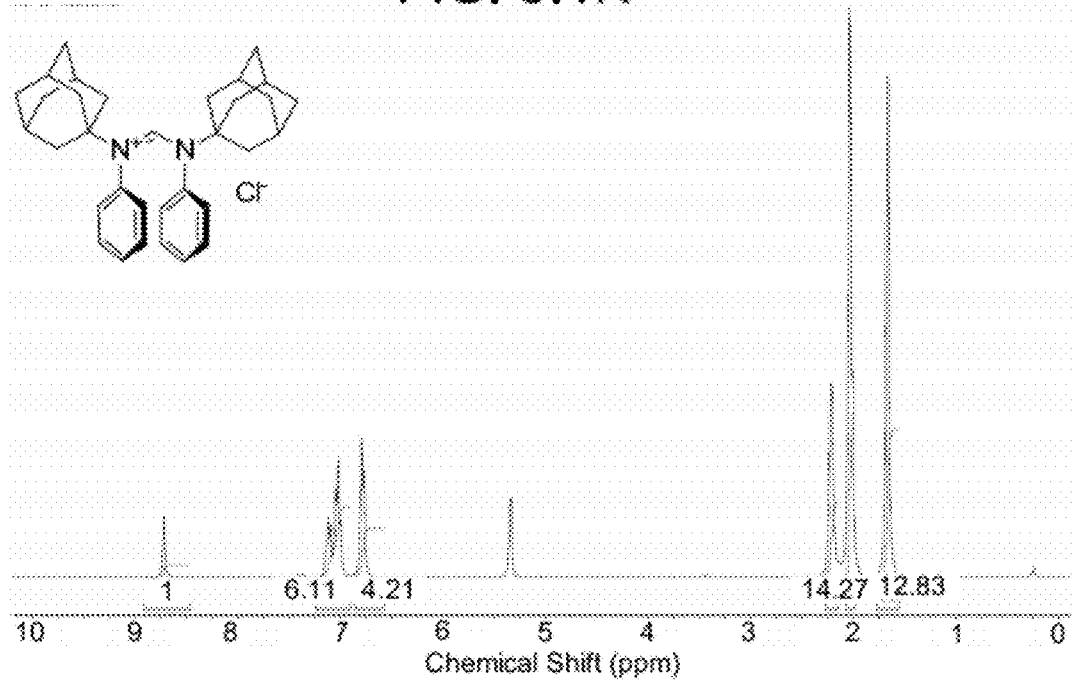
FIG. 3.1O

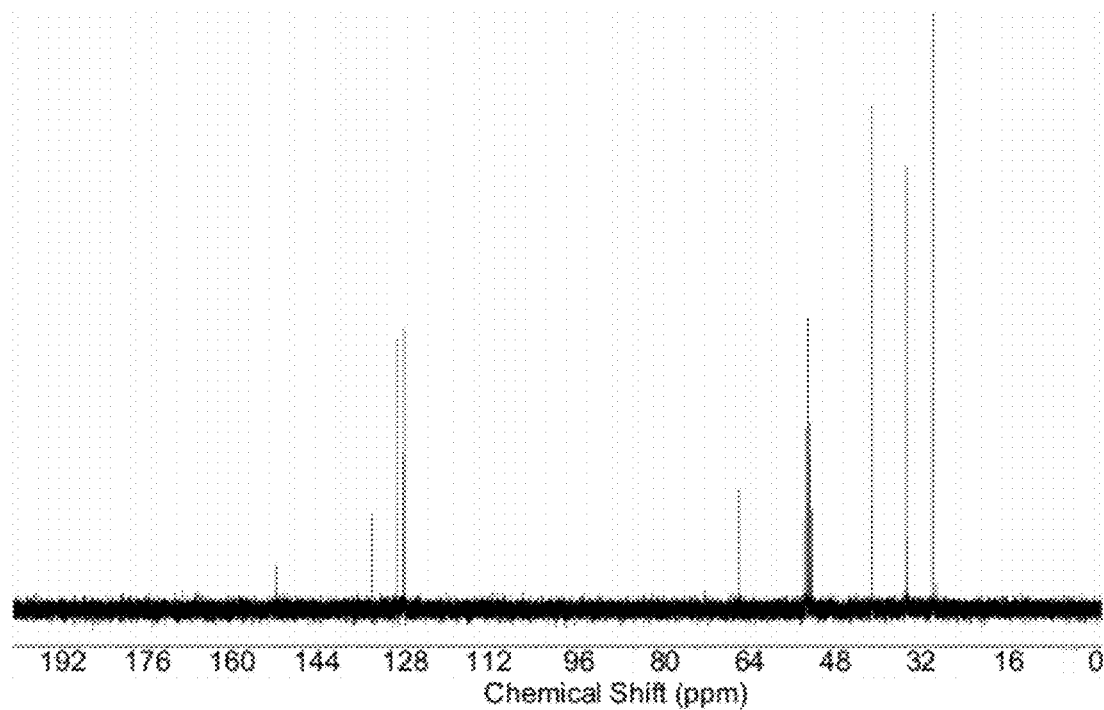
FIG. 3.1P
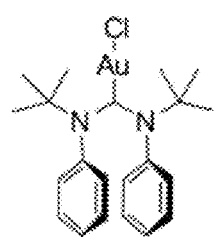
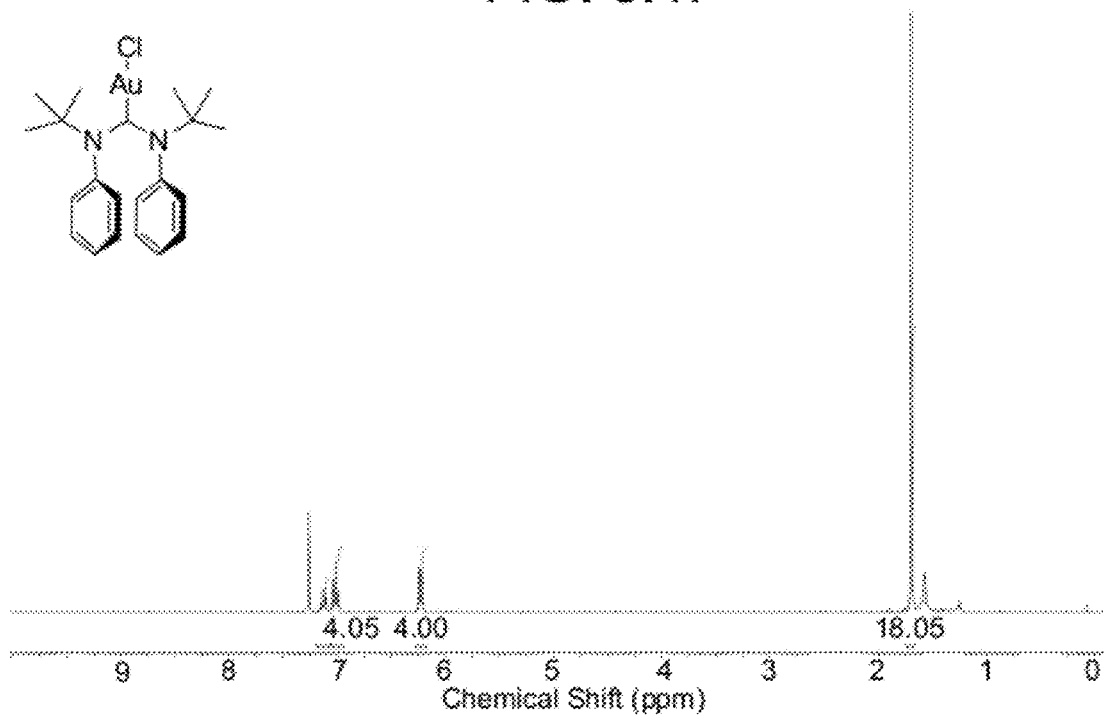
FIG. 3.1Q

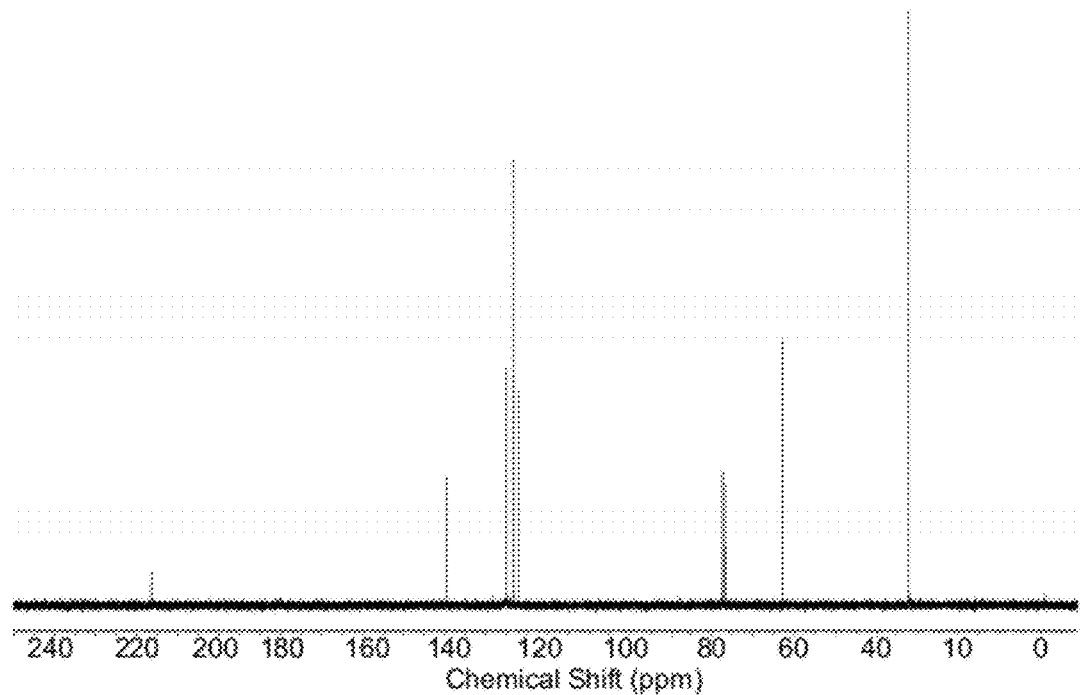
FIG. 3.1R
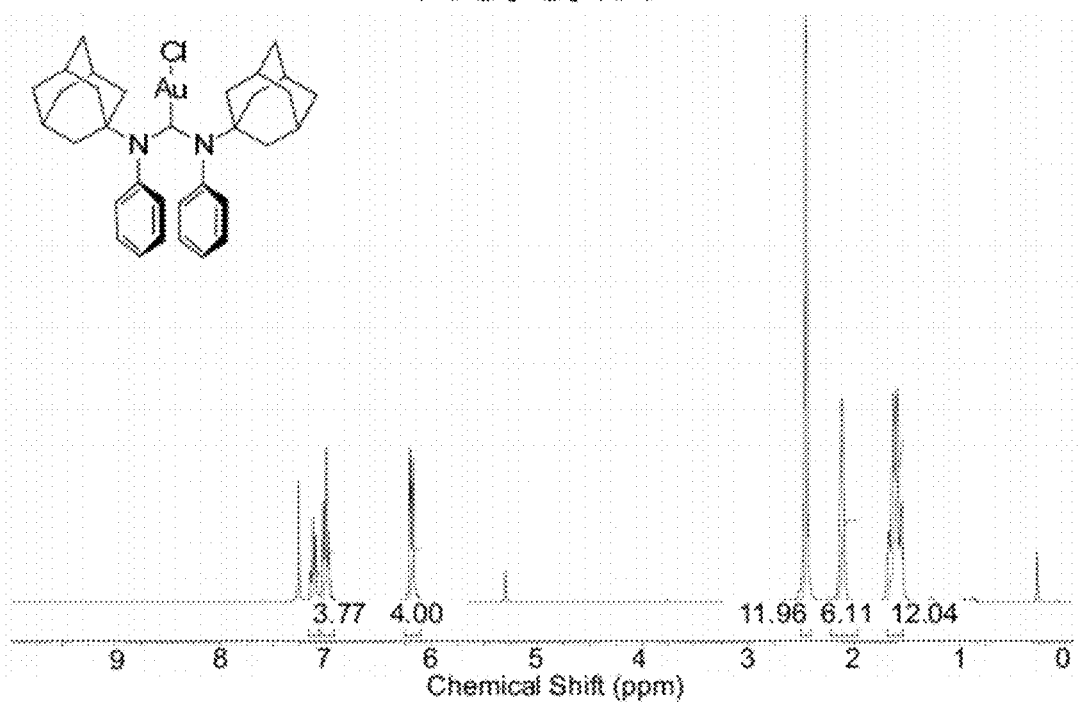
FIG. 3.1S

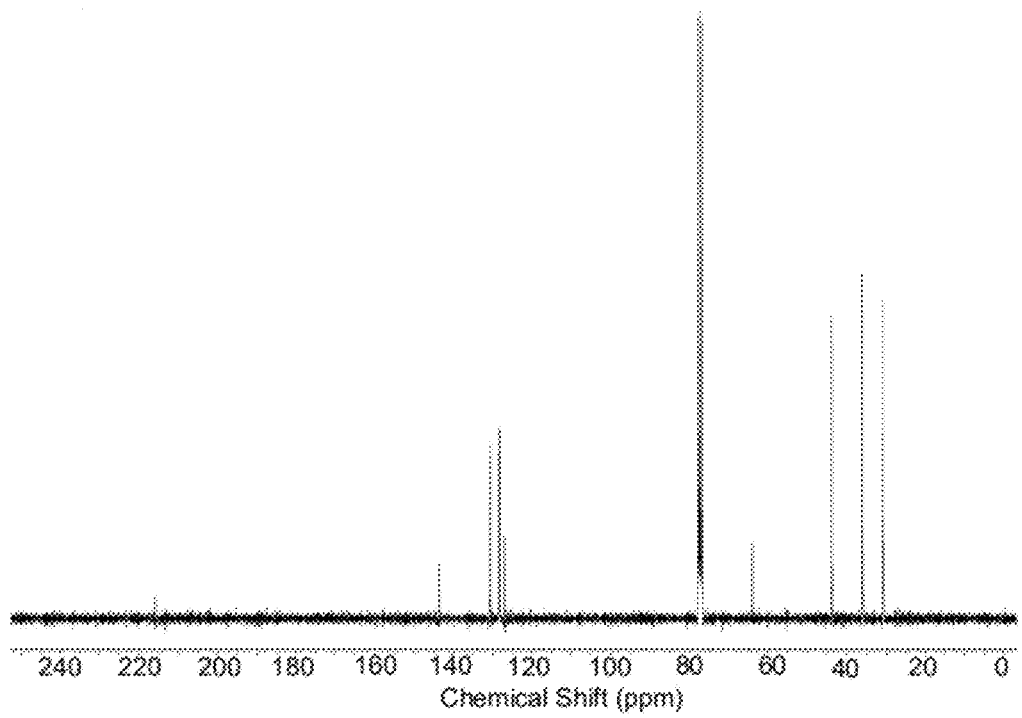
FIG. 3.1T
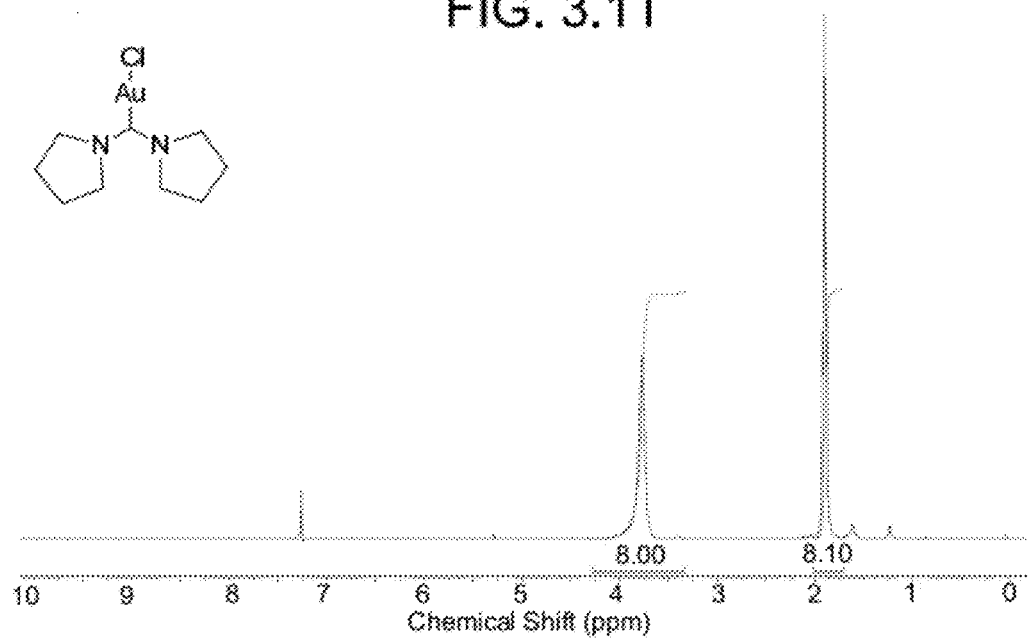
FIG. 3.1U

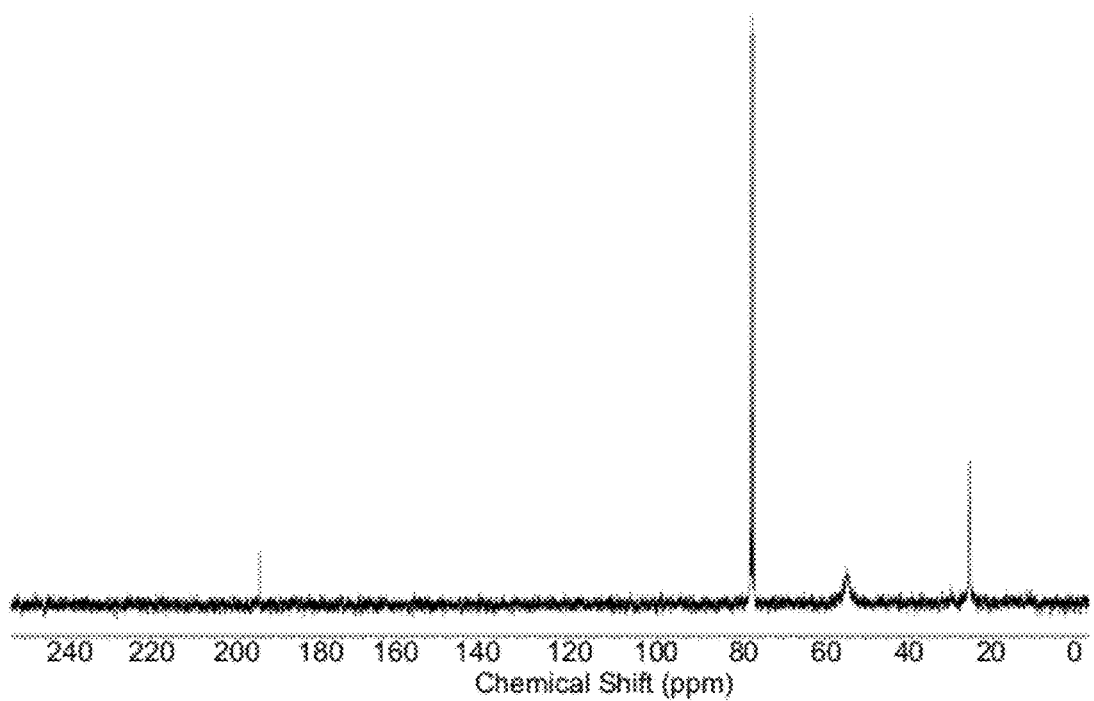
FIG. 3.1V

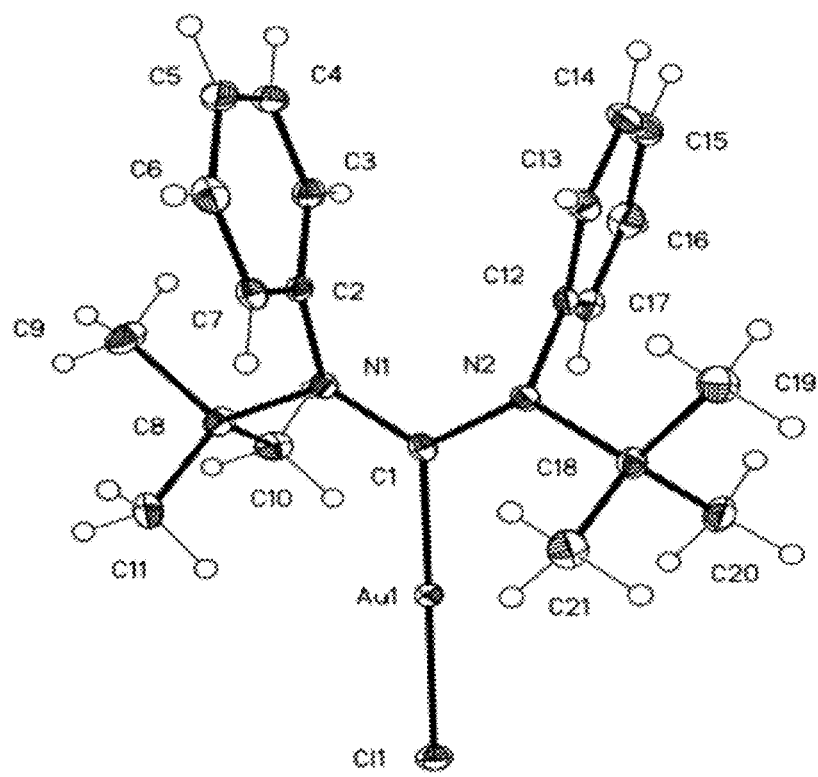
Selected bond lengths (Å), angles (°) and dihedral angles (°)
Au1–C1 2.006(3)  Au1–Cl1 2.2982(7)  C1–N1 1.348(3)  C1–N2 1.452(3)
N1–C1–N2 115.0(2)  C1–Au1–Cl1 179.01(6)  C2–N1–C1–N2 -24.3(3)
C8–N1–C1–N2 170.4(2)  C12–N2–C1–N1 -47.8(3)  C18–N2–C1–N1 160.7(2)
FIG. 3.2

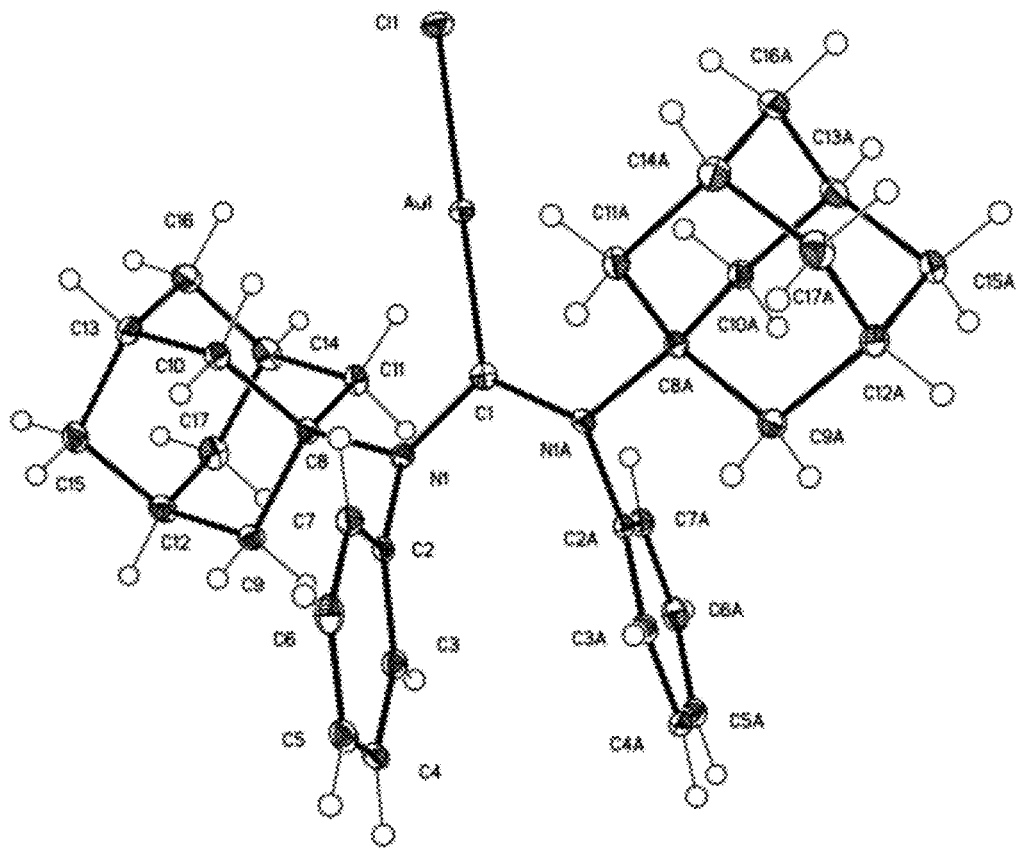
Selected bond lengths (Å), angles (°) and dihedral angles (°)
Au1-C1  2.003(2)   Au1-Cl1  2.3041(6)   C1-N1  1.371(2)
   N1-C1-N1A  113.4(2)   C1-Au1-Cl1  180.000(4)
  C8-N1-C1-N1A  163.6(2)   C2-N1-C1-N1A  -41.0(2)
FIG. 3.3

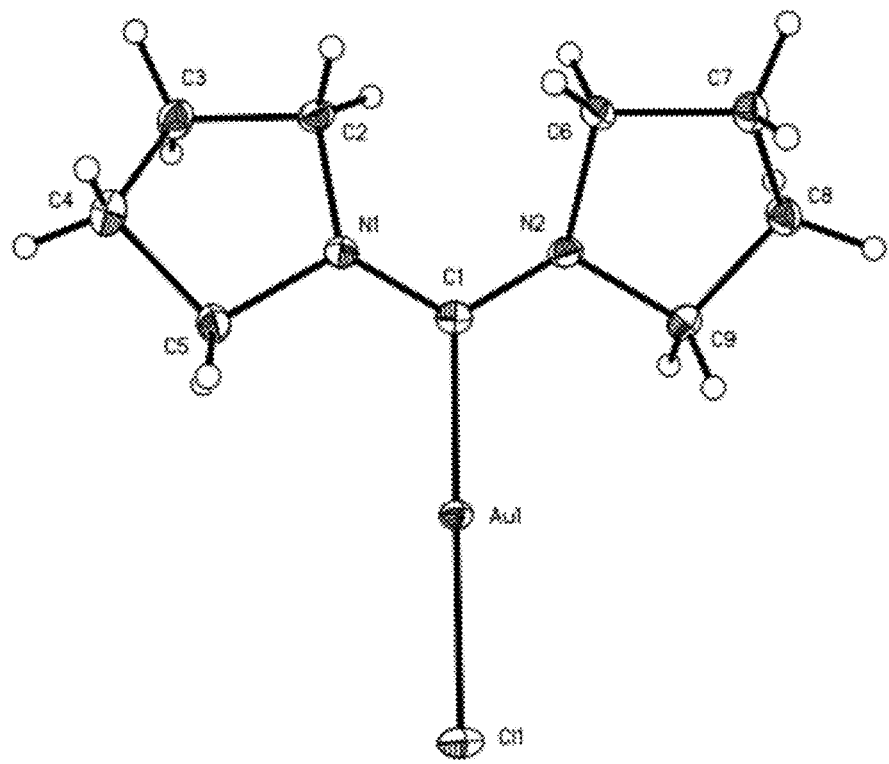
Selected bond lengths (Å), angles (°) and dihedral angles (°)
Au1–C1  2.014(2)   Au1–Cl1  2.3010(6)   C1–N1  1.334(3)   C1–N2  1.338(3)
N1–C1–N2  119.9(2)   C1–Au1–Cl1  177.93(7)   C2-N1-C1-N2  17.6(3)
C5-N1-C1-N2  -176.8(2)   C6-N2-C1-N1  26.2(3)   C9-N2-C1-N1  -170.7(2)
FIG. 3.4

US 8,530,687 B2

CATALYSTS, METHODS OF MAKING CATALYSTS, AND METHODS OF USE

CROSS-REFERENCE TO RELATED APPLICATION

This application claims priority to U.S. provisional application entitled "CATALYSTS, METHODS OF MAKING CATALYSTS, AND METHODS OF USE," having Ser. No. 61/380,359, filed on Sep. 7, 2010, which is entirely incorporated herein by reference.

STATEMENT OF GOVERNMENTAL SUPPORT

This invention was made with government support under grant number 08KN-04 awarded by the Florida Department of Health. The government has certain rights in the invention.

BACKGROUND

N-heterocyclic carbenes (NHCs) are useful ligands for various catalytic transformations, and thus there is interest in designing NHC to be used as catalysts that overcome current limitations and disadvantages.

SUMMARY

Embodiments of the present disclosure provide for acyclic diaminocarbenes (ADCs) catalysts such as those shown in FIG. 1.1 and in the Examples, methods of making catalysts, methods of using catalysts, and the like. Catalyst of the present disclosure can be useful in various catalytic transformations. Embodiments of the catalyst can be used in hydroamination, cycloisomerization, allylic rearrangement reactions, alkyne hydration reactions, Meyer-Schuster rearrangement reactions, and the like.

In an embodiment the compound, among others, includes a compound having a formula of compound A:

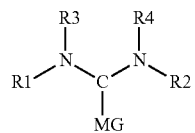

wherein R1 and R2 are independently selected from a secondary alkyl group, unsubstituted or substituted, or a tertiary alkyl group, unsubstituted or substituted, R3 and R4 are independently selected from an aryl group, and MG is a metal group.

In an embodiment the compound, among others, includes a compound having a formula of compound A:

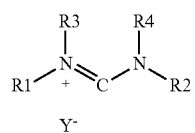

wherein R1 and R2 are independently selected from a secondary alkyl group, unsubstituted or substituted, or a tertiary alkyl group, unsubstituted or substituted, R3 and R4 are independently an aryl group, Y is selected from the group consisting of: Cl, Br, I, $BF_4$, $PF_6$, $BAr_4$, $ClO_4$, OAc, OTf, Ts, Ms, $NTf_2$, and $PO_2Cl_2$.

Other structures, methods, features, and advantages of the present disclosure will be, or become, apparent to one with skill in the art upon examination of the following drawings and detailed description. It is intended that all such additional structures, methods, features, and advantages be included within this description, be within the scope of the present disclosure, and be protected by the accompanying claims.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIG. 1.1 describes catalyst of the present disclosure and these include compound A, compound B, and compound C.

FIG. 1.2 illustrates a generic scheme for preparing compounds of the present disclosure where R1 and R2 are the same and R3 and R4 are the same.

FIG. 2.1 illustrate the sterically demanding, conformationally stable N,N'-dialkyl-N,N'-diaryl acyclic diaminocarbenes FIG. 2.2 illustrates a) X-ray structure of 5a. b) X-ray structure of 5b. Ellipsoids are drawn at the 50% probability level.

FIG. 2.3 illustrates the % $V_{Bur}$ of ADC and NHC ligands in Au complexes (calculated using X-ray crystallographic data).

FIG. 3.1A illustrates $^1$H NMR spectrum of 1a.
FIG. 3.1B illustrates $^{13}$C NMR spectrum of 1a.
FIG. 3.1C illustrates $^1$H NMR spectrum of 1a.
FIG. 3.1D illustrates $^{13}$C NMR spectrum of 1b.
FIG. 3.1E illustrates $^1$H NMR spectrum of 2a.
FIG. 3.1F illustrates $^{13}$C NMR spectrum of 2a.
FIG. 3.1G illustrates $^1$H NMR spectrum of 2b.
FIG. 3.1H illustrates $^{13}$C NMR spectrum of 2b.
FIG. 3.1I illustrates $^1$H NMR spectrum of 3a.
FIG. 3.1J illustrates $^{13}$C NMR spectrum of 3a.
FIG. 3.1K illustrates $^1$H NMR spectrum of 3b.
FIG. 3.1L illustrates $^{13}$C NMR spectrum of 3b.
FIG. 3.1M illustrates $^1$H NMR spectrum of 4a.
FIG. 3.1N illustrates $^{13}$C NMR spectrum of 4a.
FIG. 3.1O illustrates $^1$H NMR spectrum of 4b.
FIG. 3.1P illustrates $^{13}$C NMR spectrum of 4b.
FIG. 3.1Q illustrates $^1$H NMR spectrum of 5a.
FIG. 3.1R illustrates $^{13}$C NMR spectrum of 5a.
FIG. 3.1S illustrates $^1$H NMR spectrum of 5b.
FIG. 3.1T illustrates $^{13}$C NMR spectrum of 5b.
FIG. 3.1U illustrates $^1$H NMR spectrum of 5c.
FIG. 3.1V illustrates $^{13}$C NMR spectrum of 5c.

FIG. 3.2 illustrates X-ray structure of 5a and selected bond lengths and angles. Ellipsoids are drawn at the 50% probability level.

FIG. 3.3 illustrates X-ray structure of 5b and selected bond lengths and angles. Ellipsoids are drawn at the 50% probability level.

FIG. 3.4 illustrates X-ray structure of 5c and selected bond lengths and angles. Ellipsoids are drawn at the 50% probability level.

DETAILED DESCRIPTION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of medicine, organic chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

DEFINITIONS

The term "substituted" refers to any one or more hydrogens on the designated atom compound that can be replaced with a selection from the indicated group, provided that the designated atom's normal valence is not exceeded, and that the substitution results in a stable compound. The use of the term "substituted" can indicate that one or more of the hydrogens on a carbon or carbon chain (e.g., include more than one carbon atom) can be replaced.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

As used herein, "alkenyl" or "alkenyl group" refers to an aliphatic hydrocarbon radical which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "arylalkyl" refers to an arylalkyl group wherein the aryl and alkyl are as herein described. Examples of arylalkyl include, but are not limited to, -phenylmethyl, -phenylethyl, -phenylpropyl, -phenylbutyl, and -phenylpentyl.

The term "alkynyl" refers to straight or branched chain hydrocarbon groups having 2 to 12 carbon atoms, preferably 2 to 4 carbon atoms, and at least one triple carbon to carbon bond, such as ethynyl. An alkynyl group is optionally substituted, unless stated otherwise, with one or more groups, selected from aryl (including substituted aryl), heteroaryl, heterocyclo (including substituted heterocyclo), carbocyclo (including substituted carbocyclo), halo, hydroxy, alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, lactam, urea, urethane, sulfonyl, and the like.

The term "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. The term "lower alkoxy" means an alkoxy group having less than 10 carbon atoms.

The term "cycloalkyl" refers to a non-aromatic mono- or multicyclic ring system of about 3 to about 10 carbon atoms, preferably of about 5 to about 10 carbon atoms. Preferred ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

The term "cycloalkenyl" refers to a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. Exemplary monocyclic cycloalkenyl include cyclopentenyl, cyclohexenyl, cycloheptenyl, and the like. An exemplary multicyclic cycloalkenyl is norbornylenyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

The term "biaryl" refers to an aryl, as defined above, where two aryl groups are joined by a direct bond or through an intervening alkyl group, preferably a lower alkyl group.

The term "fused aryl" refers to a multicyclic ring system as included in the term "aryl," and includes aryl groups and heteroaryl groups that are condensed. Examples are naphthyl, anthryl and phenanthryl. The bonds can be attached to any of the rings.

"Aralkyl" and "heteroaralkyl" refer to aryl and heteroaryl moieties, respectively, that are linked to a main structure by an intervening alkyl group, e.g., containing one or more methylene groups.

The term "fluorobenzyl" refers to a benzyl group wherein the phenyl moiety is substituted with one or more fluorine atoms, including 2, 3, 4 and 5 fluorine atom substituents.

Similarly, "halobenzyl" refers to benzyl substituted with one or more different halogens, including fluorine, chlorine, bromine, and iodine.

The term "substituted," as in "substituted alkyl," "substituted cycloalkyl," "substituted cycloalkenyl," substituted aryl," substituted biaryl," "substituted fused aryl" and the like means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

To the extent that the disclosed compounds, and salts thereof, may exist in their tautomeric form, all such tautomeric forms are contemplated herein as part of the present disclosure.

All stereoisomers of the compounds of the present disclosure, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

DISCUSSION

Embodiments of the present disclosure provide for acyclic diaminocarbenes (ADCs) catalysts such as those shown in FIG. 1.1 and in the Examples, methods of making catalysts, methods of using catalysts, and the like. Catalyst of the present disclosure can be useful in various catalytic transformations. Embodiments of the catalyst can be used in hydroamination, cycloisomerization, allylic rearrangement reactions, alkyne hydration reactions, Meyer-Schuster rearrangement reactions, and the like. Additional details are described in the Example section.

FIG. 1.1 describes an ADC catalyst of the present disclosure and these include compound A, compound B, and compound C. Compound A is a general formula of compounds of the present disclosure, while compound B (R3 and R4 are Ph groups) and compound C(R3 and R4 are Ph groups and MG is AuCl) are specific embodiments of compounds of the present disclosure. Compounds A, B, and C are conformationally stable in that they retain one conformation and do not switch like other compounds during catalysis. Although not intending to be bound by theory, it is postulated that the bulk of the groups (R1, R2, R3, and/or R4) contributes to the conformational stability of compounds A-C. In addition, compounds A, B, and C are sterically demanding in that certain bonds cannot be accessed by $S_N2$ reaction pathways. See the Example section for additional details.

R1 and R2 are each independently selected and can be the same or different. In an embodiment, R1 and R2 can be a bulky group and are sterically demanding. In an embodiment, R1 and R2 can not be accessed by $S_N2$ reaction pathways. In an embodiment, R1 and R2 can each be a secondary alkyl group (unsubstituted or substituted) or a tertiary alkyl group (unsubstituted or substituted). In particular, R1 and R2 can be independently selected from one of the following groups: tert-butyl, adamantyl, isopropyl, cyclopentyl, cyclohexyl, cycloheptyl, cyclooctyl, 1-phenylethyl, 1-cyclohexylethyl, 1-(1-naphthyl)ethyl, 1-(tert-butyl)ethyl, and 1-(o-methoxyphenyl)ethyl, any of which can be unsubstituted or substituted. In two embodiments, R1 and R2 are the same and can be either tert-butyl groups or adamantyl groups.

R3 and R4 are each independently selected and can be the same or different. In an embodiment, R3 and R4 can be a bulky group and are sterically demanding. In an embodiment, R3 and R4 can be an aryl group (unsubstituted or substituted). In particular, R3 and R4 can be independently selected from one of the following groups: phenyl (Ph), 1-naphthyl, 2-naphthyl, 2-alkylphenyl, 2-alkoxyphenyl, 2-halophenyl, 2-arylphenyl, 4-alkylphenyl, 4-alkoxyphenyl, 4-halophenyl, 4-arylphenyl, 3,5-dialkylphenyl, 3,5-dialkoxyphenyl, 3,5-dihalophenyl, and 3,5-diarylphenyl, any of which can be unsubstituted or further substituted. In two embodiments, R1 and R2 are the same and can be a phenyl group.

MG refers to a metal group. In an embodiment, M can be a metal that can be used in a catalytic reaction. In an embodiment, M can be a metal such as Au, Pt, Ir, Rh, Re, Ru, Ni, Pd, Cu, Fe, and Co. G can be one or more (depending on the charge of the metal ion) halogens, cyanide, alkenes, dienes, alkynes, allyls, alkyls, aryls, alcohols, amines, phosphines, carbonyls, nitriles, isonitriles (isocyanides), isocyanates or a combination thereof. In an embodiment MG can be selected from the following: AuCl, AuCN, Ir(COD)Cl, Rh(COD)Cl, Ir(CO)$_2$Cl and Rh(CO)$_2$Cl. In an embodiment MG can be AuCl.

FIG. 1.2 illustrates a generic scheme for preparing compounds of the present disclosure where R1 and R2 are the same and R3 and R4 are the same. Additional details regarding a specific synthesis scheme are described in the Examples. FIG. 1.2 illustrates that compound 5 is reacted with HC(O)OAc in a solvent (e.g., THF, methylene chloride, acetone, chloroform, toluene) for about 5 to 9 hours at about room temperature to form compound 10. Then compound 10 is reacted with oxalyl chloride, trifluoromethanesulfonic anhydride, or phosphoryl chloride in a solvent (e.g., toluene, methylene chloride, chloroform, THF) for about 1 to 3 hours at about −78° C. to room temperature to form compound 15. Compound 15 is reacted with silylamines in a solvent (e.g., methylene chloride, toluene, chloroform, THF) for about 1 to 3 hours at about −78° C. to room temperature to form compound 20. Compound 20 is reacted with NH4Y or NaY or KY or AgY (Y is defined in FIG. 1.2) in a solvent (e.g., acetone or methylene chloride) at about room temperature for about 1 to 12 hours. Compound 22 is reacted with LiHMDS (lithium hexamethyldisilazide), NaHMDS (sodium hexamethyldisilazide) in a solvent (e.g., THF, diethyl ether) for about 10 to 60 min at about −78° C. and then reacted with Me$_2$S.AuCl in a solvent (e.g., THF, diethyl ether) for about 0.5 to 3 hours at about −78° C. to room temperature to form compound 25.

As noted above, catalysts of the present disclosure can be used in various reactions such as the following:

Hydroamination, where X is OCH$_2$Ph or NHPh; n=1, 2, or 3; R10, R11 and R12 are hydrogen, alkyl groups or aryl groups.

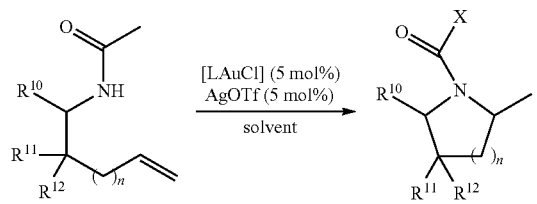

X = OCH$_2$Ph or NHPh
n = 1, 2, or 3
R$^{10}$, R$^{11}$, R$^{12}$ = H, alkyl or aryl groups Cycloisomerization

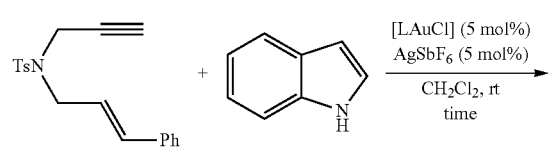

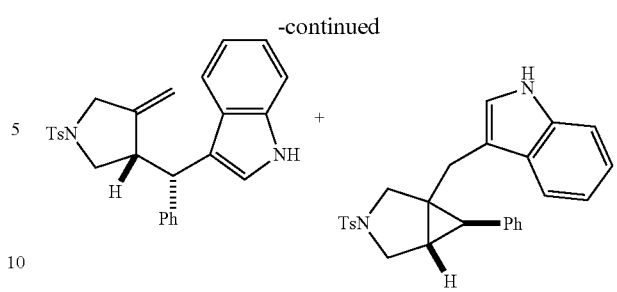

Allylic rearrangement

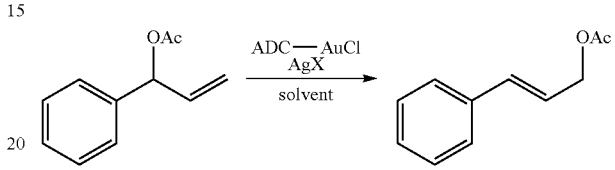

Alkyne hydration, where R13 and R14 are alkyl groups or aryl groups.

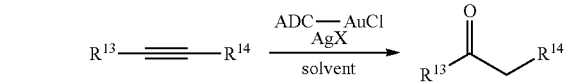

Meyer-Schuster rearrangement, where R15, R16 and R17 are alkyl groups or aryl groups.

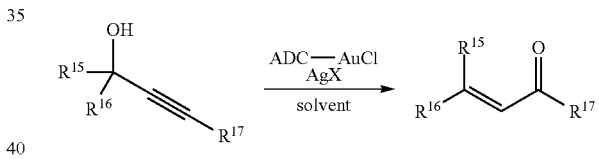

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Example 1

N-heterocyclic carbenes (NHCs) are useful ligands for various catalytic transformations, which is often attributed to their σ-donating capacity as well as tunable steric profile.[i] Recently, acyclic diaminocarbenes (ADCs) have emerged as interesting ligands, as they show unique electronic and steric parameters.[ii] Without geometric constraint, ADCs feature a broader variation of the N—C$_{carbene}$—N angle as well as free rotation about the C$_{carbene}$—N bonds.[iia] Previous reports indicate that ADCs are more electron-donating than NHCs.[iio,iip] Additionally, one might expect that ADCs' typically wider N—C$_{carbene}$—N angle can increase steric encumbrance at the metal coordination sphere. Nevertheless, the development of ADCs has lagged behind that of NHCs. ADCs tend to be less stable than NHCs, as they dimerize easily and are more vulnerable to moisture and oxygen.[ii,iii] Control of rotational freedom in differentially substituted ADCs could be an issue, e.g., to design chiral ADC ligands. Steric bulk is essential to protect carbene carbons from dimerization as well as moisture or oxygen,[iii] and popular NHC ligands such as IMes or IPr are typically equipped with a high level of steric encumbrance. However, to the best of our knowledge, there are no such ADCs displaying similar level of steric demands.[ii,iii,iv] We envisioned that introduction of bulky alkyl substituents to N,N'-diaryl ADCs[v] could result in increasing the steric demands as well as limiting conformations (FIG. 2.1). Herein we report synthesis of novel bulky ADC ligands and their application in gold-catalysis.

N,N'-diaryl ADCs were first developed by Bielawski and co-workers, and the formamidinium ADC precursors were nicely prepared by the double $S_N2$ alkylation of N,N'-diarylformamidine with 2 equivalents of alkyl halide.[vc] However, the $S_N2$ alkylation strategy is not applicable to the synthesis of N,N'-diaryl ADCs bearing tertiary alkyl groups. We were pleased to find that reactions of silylated amines with chloroiminiums afforded the desired hindered formamidiniums (4a,b) in high yield (Scheme 1). TMS—Cl (chlorotrimethylsilane) elimination protocol for the synthesis of formamidiniums, which was originally developed by Schroth[vi] provides a distinct advantage over the common procedure using free amines. TMS—Cl is the only by-product and can be easily removed by evaporation or washing with hydrocarbon solvents, whereas HCl generated from the conventional procedure can complicate the product isolation from other by-products such as amine-HCl salts.[iiq] Two novel ADC-gold complexes (5a,b) were then prepared by deprotonation of formamidiniums (4a,b) with $LiN(SiMe_3)_2$ followed by metalation using $Me_2S.AuCl$.

The X-ray structure of 5a and 5b shows "anti" conformation where both phenyl rings are located away from the gold metal (FIG. 2.2). The two phenyl rings in 5a and 5b adopt a face-to-face, parallel-displaced stacking arrangement, implying possible π-π interactions.[vii] It is also interesting to note that both phenyl rings are twisted out of the $N$—$C_{carbene}$—$N$ plane, shown by relatively large $C_{phenyl}$—$N$—$C_{carbene}$—$N$ dihedral angles (−24.3(3)°, −47.8(3)° for 5a and −41.0(2)° for 5b). These geometries might be preferred to accommodate bulky tertiary alkyl substituents but could result in weakening π-overlap between nitrogens and the carbene carbon. The buried volume (% $V_{Bur}$)[viii,ix] of 5a (44.3%) is larger than that of similarly substituted NHC—Au complex 5f (39.3%), possibly owing to larger $N$—$C_{carbene}$—$N$ angle of 5a (115.0(2)°) than that of 5f (107.8(2)°) (FIG. 2.3). Importantly, bulkier adamantyl substituent further increases % $V_{Bur}$ of 5b to 45.7%, which constitutes one of the highest among the reported ADC ligands and is comparable to that of bulky NHCs such as IPr (45.6%).

Electron-donating capacities of the new ADCs were estimated by density functional theory (DFT) calculations (Table 1). The energies of the carbene lone pair orbital ($E_o$) were computed, after an initial geometry optimization, using the B3LYP,[x] TPSSTPSS,[xi] M06[xii] and M06L[xiii] functional and the 6-31G** basis set[xiv] on carbenes 6a-d and 6f,g. These calculations were run using GAUSSIAN 09.[xv] The ADCs (6a-d) have higher $E_o$ values than the NHCs (6f,g), suggesting that they are better σ-donors. The same trends were observed across the carbenes for all four functionals.

TABLE 1

Energies of carbene lone pair orbitals, $E_o$ [eV].

|  | 6a | 6b | 6c | 6d | 6f | 6g |
|---|---|---|---|---|---|---|
| B3LYP | −4.59 | −4.57 | −4.42 | −4.86 | −5.25 | −5.61 |
| TPSS | −3.74 | −3.71 | −3.53 | −3.95 | −4.34 | −4.69 |
| M06 | −4.95 | −4.94 | −4.73 | −5.20 | −5.59 | −6.06 |
| M06L | −3.91 | −3.88 | −3.66 | −4.13 | −4.52 | −4.99 |

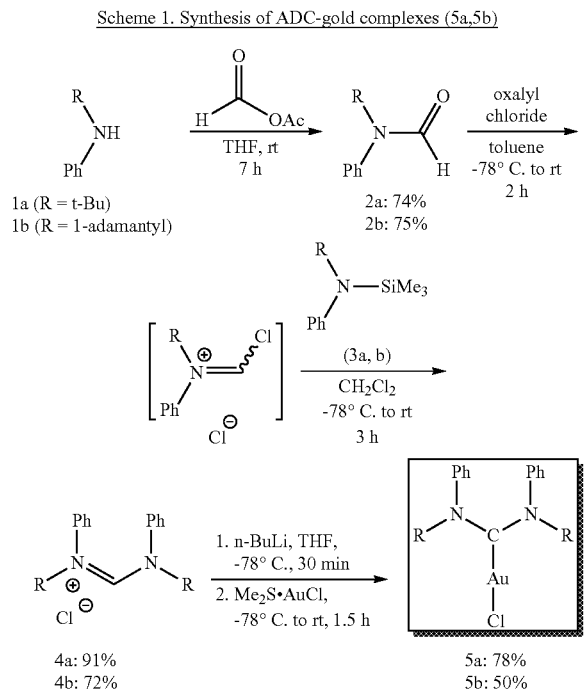

Scheme 1. Synthesis of ADC-gold complexes (5a,5b)

Phosphines and NHC ligands play a crucial role in Au-catalyzed reactions where very different reactivities as well as selectivities were often observed depending on ligands.[xvi] Thus, we decided to evaluate new ADC-gold complexes 5a and 5b in representative Au-catalyzed reactions to gain insights on their properties. First, Au(I)-catalyzed intramolecular hydroamination was investigated (Table 2).[xvii] The reaction proceeded smoothly at room temperature when catalyzed by ADC—Au catalyst 5a (entry 1). The bulkier adamantyl catalyst 5b gave better conversion after 24 h (entry 2 vs entry 1), whereas less bulky ADC catalyst 5c and 5d didn't show noticeable product formation after 24 h (entry 3 and 4). There seems to be a good correlation between the steric bulk of the carbene ligands (% $V_{Bur}$) and the hydroamination rate, although steric parameters alone cannot fully explain the reactivity difference between 5b and 5g. Although sterics are known to be important for an aminoauration step,[xviiia] the rate of protodeauration could be also affected by the ligand electronics.[xviiib] It is also interesting to note that recently reported N,N'-disubstituted ADC-gold complex (5e) was not very effective in hydroamination at room temperature, even though 5e also has two t-Bu groups facing toward the Au metal center (entry 5).

diaryl ADCs might have very unique properties compared to other carbene ligands. It is possible that such ADCs could be more π-accepting than the NHC counterparts, resulting from the larger $C_{phenyl}$—N—$C_{carbene}$—N dihedral angle,[xx] even though ADCs are generally better σ-donors than NHCs. This selectivity reversal could be rationalized by the more π-accepting nature of bulky diaryl ADCs rendering the carbenoid intermediate (B) less favorable. However, more detailed studies on electronic properties of these bulky ADC ligands must be done before drawing any generalized conclusion.

To summarize, sterically demanding and conformationally stable N,N'-dialkyl-N,N'-diaryl ADCs featuring tertiary alkyl substituents were developed. The formamidinium precursors were efficiently prepared via TMS—Cl elimination route, and X-ray structures of Au complexes confirmed that the new diaryl ADCs show steric demands comparable to IPr. The ADC—Au catalysts not only showed competitive reactivities in hydroamination and enyne cyclization, but also demonstrated unique ligand properties different from bulky NHC counterparts or other acyclic carbenes.

TABLE 2

Au(I)-catalyzed hydroamination of alkenyl urea[a]

| entry | catalyst | % $V_{Bur}$ | time (h) | % convn[b] |
|---|---|---|---|---|
| 1 | tBu$_2$Ph$_2$ADC—AuCl (5a) | 44.3 | 24 | 82 |
| 2 | Adm$_2$Ph$_2$ADC—AuCl (5b) | 45.7 | 24 | 87[c] |
| 3 | Pyrr$_2$ADC—AuCl (5c) | 29.5 | 24 | <2 |
| 4 | Et$_2$tBuHADC—AuCl (5d) | 36.0 | 24 | <2 |
| 5 | tBu$_2$H$_2$ADC—AuCl (5e) | 39.2 | 24 | 3 |
| 6 | ItBu—AuCl (5f) | 39.3 | 24 | 3 |
| 7 | IPr—AuCl (5g) | 45.6 | 16 | >98 |

[a]0.033M concd [LAuCl] and AgOTf in dioxane were stirred for 30 min before addition of 7.
[b]Determined by $^1$H NMR.
[c]>98% conversion observed after 48 h.

In Au(I)-catalyzed indole addition to 1,6-enyne, the product ratio is known to vary greatly depending on the ligand electronic and steric properties.[xix] Previous reports showed that sterically bulky phosphite-Au complexes yielded 10 as the major product, whereas sterically bulky NHC—Au complexes yielded mainly 11.[xix] New bulky diaryl ADC—Au complexes (5a,b) gave good yields (76-78%), showing similar reactivity as IPr—Au catalyst (Table 3). Note that bulky diaryl ADC—Au catalyst 5b prefers the alkene product 10 (entry 2), whereas similarly bulky NHC—Au catalyst 5g favors the cyclopropane product 11 (entry 7). The dramatic reversal of product distribution exhibited by similarly encumbered catalysts 5b and 5g seems to suggest that new bulky

TABLE 3

Indole addition to 1,6-enyne catalyzed by Au(I)[a]

| entry | catalyst | time (h) | % yield[b] | 10/11[c] |
|---|---|---|---|---|
| 1 | tBu$_2$Ph$_2$ADC—AuCl (5a) | 3 | 76 | 51/49 |
| 2 | Adm$_2$Ph$_2$ADC—AuCl (5b) | 3 | 78 | 82/18 |
| 3 | Pyrr$_2$ADC—AuCl (5c) | 5 | 0 | — |
| 4 | Et$_2$tBuHADC—AuCl (5d) | 3 | 45 | 46/54 |
| 5 | tBu$_2$H$_2$ADC—AuCl (5e) | 3 | 22 | 46/54 |
| 6 | ItBu—AuCl (5f) | 3 | 67 | 43/57 |
| 7 | IPr—AuCl (5g) | 3 | 75 | 26/74 |

[a]0.075M concd [LAuCl] and AgSbF$_6$ in CH$_2$Cl$_2$ were stirred for 15 min before addition of 9 and indole.
[b]Isolated yield of the mixture of 10 and 11. Average of 2 runs.
[c]Determined by $^1$H NMR. Average of 2 runs.

References for Example 1, Each of which is Incorporated Herein by Reference (The Number or the Corresponding Roman Numeral are Noted in the Text)

(1) (i) (a) Diez-González, S.; Marion, N.; Nolan, S. P. *Chem. Rev.* 2009, 109, 3612-3676. (b) Hahn, F. E.; Jahnke, M. C. *Angew. Chem., Int. Ed.* 2008, 47, 3122-3172. (c) Glorius, F. *Top. Organomet. Chem.* 2007, 21, 1-20. (d) *N-heterocyclic Carbenes in Synthesis*; Nolan, S. P., Ed.; Wiley-VCH: Weinheim, 2006.

(2) (ii) (a) Vignolle, J.; Cattoën, X.; Bourissou, D. *Chem. Rev.* 2009, 109, 3333-3384. (b) Slaughter, L. M. *Comments Inorg. Chem.* 2008, 29, 46-72. (c) Snead, D. R.; Inagaki, S.; Abboud, K. A.; Hong, S. *Organometallics* 2010, 29, 1729-1739. (d) Snead, D. R.; Ghiviriga, I.; Abboud, K. A.; Hong, S. *Org. Lett.* 2009, 11, 3274-3277. (e) Hirsch-Weil, D.; Snead, D. R.; Inagaki, S.; Seo, H.; Abboud, K. A.; Hong, S. *Chem. Commun.* 2009, 2475-2477. (f) Kremzow, D.; Seidel, G.; Lehmann, C. W.; Fürstner, A. *Chem. Eur. J.* 2005, 11, 1833-1853. (g) Bartolomé, C.; García-Cuadrado, D.; Ramiro, Z.; Espinet, P. *Inorg. Chem.* ASAP, DOI: 10.1021/ic101059c. (h) Bartolomé, C.; García-Cuadrado, D.; Ramiro, Z.; Espinet, P. *Organometallics* 2010, 29, 3589-3592. (i) Bartolomé, C.; Ramiro, Z.; García-Cuadrado, D.; Pérez-Galán, P.; Raducan, M.; Bour, C.; Echavarren, A. M.; Espinet, P. *Organometallics* 2010, 29, 951-956. (j) Bartolomé, C.; Ramiro, Z.; Pérez-Galán, P.; Bour, C.; Raducan, M.; Echavarren, A. M.; Espinet, P. *Inorg. Chem.* 2008, 47, 11391-11397. (k) Wanniarachchi, Y. A.; Subramanium, S. S.; Slaughter, L. M. *J. Organomet. Chem.* 2009, 694, 3297-3305. (l) Wanniarachchi, Y. A.; Slaughter, L. M. *Organometallics* 2008, 27, 1055-1062. (m) Wanniarachchi, Y. A.; Kogiso, Y.; Slaughter, L. M. *Organometallics* 2008, 27, 21-24. (n) Moncada, A. I.; Manne, S.; Tanski, J. M.; Slaughter, L. M. *Organometallics* 2006, 25, 491-505. (o) Frey, G. D.; Herdtweck, E.; Herrmann, W. A. *J. Organomet. Chem.* 2006, 691, 2465-2478. (p) Denk, K.; Sirsch, P.; Herrmann, W. A. *J. Organomet. Chem.* 2002, 649, 219-224. (q) Alder, R. W.; Blake, M. E.; Bufali, S.; Butts, C. P.; Orpen, A. G.; Schütz, J.; Williams, S. J. *J. Chem. Soc. Perkin Trans.* 1 2001, 1586-1593. (r) Alder, R. W.; Allen, P. R.; Murray, M.; Orpen, A. G. *Angew. Chem., Int. Ed.* 1996, 35, 1121-1123.

(3) (iii) Alder, R. W.; Blake, M. E.; Chaker, L.; Harvey, J. N.; Paolini, F.; Schütz, J. *Angew. Chem., Int. Ed.* 2004, 43, 5896-5911.

(4) (iv) Hashmi, A. S. K.; Hengst, T.; Lothschütz, C.; Rominger, F. *Adv. Synth. Catal.* 2010, 352, 1315-1337.

(5) (v) (a) Collins, M. S.; Rosen, E. L.; Lynch, V. M.; Bielawski, C. W. *Organometallics* 2010, 29, 3047-3053. (b) Rosen, E. L.; Sung, D. H.; Chen, Z.; Lynch, V. M.; Bielawski, C. W. *Organometallics* 2010, 29, 250-256. (c) Rosen, E. L.; Sanderson, M. D.; Saravanakumar, S.; Bielawski, C. W. *Organometallics* 2007, 26, 5774-5777.

(6) (vi) (a) Cattoën, X.; Miqueu, K.; Gornitzka, H.; Bourissou, D.; Bertrand, G. *J. Am. Chem. Soc.* 2005, 127, 3292-3293. (b) Sheludvakav, V. D.; Belvakova, Z. L.; Shevchenko, V. M.; Chemvshev, E. A. *Russ. Chem. Bull. (Engl. Transl.)* 1997, 46, 997-1002; *Izv. Akad. Nauk. SSSR, Ser. Khim.* 1997, 1035-1040. (c) W. Schroth, U. Jahn, D. Ströhl, *Chem. Ber.* 1994, 127, 2013-2022. (d) Jahn, U.; Schroth, W. *Tetrahedron Lett.* 1993, 34, 5863-5866.

(7) (vii) Meyer, E. A.; Castellano, R. W.; Diederich, F. *Angew. Chem., Int. Ed.* 2003, 42, 1210-1250.

(8) (viii) For detailed calculations, see the Supporting Information.

(9) (ix) For explanation of % $V_{Bur}$ (a measure of the space occupied by the ligand in the metal coordination sphere), see: Poater, A.; Cosenza, B.; Correa, A.; Giudice, S.; Ragone, F.; Scarano, V.; Cavallo, L. *Eur. J. Inorg. Chem.* 2009, 1759-1766.

(10) (x) (a) Becke, A. D. *J. Chem. Phys.* 1993, 98, 5648-5652. (b) Lee, C.; Yang, W.; Parr, R. G. *Phys. Rev. B* 1988, 37, 785-789. (c) Vosko, S. H.; Wilk, L.; Nusair, M. *Can. J. Phys.* 1980, 58, 1200-1211. (d) Stephens, P. J.; Devlin, F. J.; Chabalowski, C. F.; Frisch, M. J. *J. Chem. Phys.* 1994, 98, 11623-11627.

(11) (xi) Tao, J.; Perdew, J. P.; Staroverov, V. N.; Scuseria, G. E. *Phys. Rev. Lett.* 2003, 91, 146401.

(12) (xii) Zhao, Y.; Truhlar, D. G. *Theor. Chem. Acc.* 2008, 120, 215-241.

(13) (xiii) Zhao, Y.; Truhlar, D. G. *J. Chem. Phys.* 2006, 125, 194101.

(14) (xiv) (a) Ditchfield, R.; Hehre, W. J.; Pople, J. A. *J. Chem. Phys.* 1971, 54, 724-728. (b) Hehre, W. J.; Ditchfield, R.; Pople, J. A. *J. Chem. Phys.* 1972, 56, 2257-2261. (c) Hariharan, P. C.; Pople, J. A. *Theor. Chem. Acc.* 1973, 28, 213-222. (d) Hariharan, P. C.; Pople, J. A. *Mol. Phys.* 1974, 27, 209-214. (e) Francl, M. M.; Pietro, W. J.; Hehre, W. J.; Binkley, J. S.; Gordon, M. S.; DeFrees, D. J.; Pople, J. A. *J. Chem. Phys.* 1982, 77, 3654-3665.

(15) (xv) Gaussian 09, Revision A.02, Frisch, M. J. et. al. Gaussian, Inc., Wallingford, Conn., USA, 2009. See supporting Information for a full list of the authors.

(16) (xvi) (a) Gorin, D. J.; Sherry, B. D.; Toste, F. D. *Chem. Rev.* 2008, 108, 3351-3378. (b) Jiménez-Núñez, E.; Echavarren, A. M. *Chem. Rev.* 2008, 108, 3326-3350. (c) Li, Z.; Brouwer, C.; He, C. *Chem. Rev.* 2008, 108, 3239-3265. (d) Marion, N.; Nolan, S. P. *Chem. Soc. Rev.* 2008, 37, 1776-1782. (e) Alcarazo, M.; Stork, T.; Anoop, A.; Thiel, W.; Fürstner, A. *Angew. Chem., Int. Ed.* 2010, 49, 2542-2546. (f) Benitez, D.; Tkatchouk, E.; Gonzalez, A. Z.; Goddard III, W. A.; Toste, F. D. *Org. Lett.* 2009, 11, 4798-4801.

(17) (xvii) (a) Li, H.; Widenhoefer, R. A. *Org. Lett.* 2009, 11, 2671-2674. (b) Bender, C. F.; Widenhoefer, R. A. *Chem. Commun.* 2008, 2741-2743. (c) Zhang, Z.; Bender, C. F.; Widenhoefer, R. A. *J. Am. Chem. Soc.* 2007, 129, 14148-14149. (d) Zhang, Z.; Bender, C. F.; Widenhoefer, R. A. *Org. Lett.* 2007, 9, 2887-2889. (e) Zhang, Z.; Liu, C.; Kinder, R. E.; Han, X.; Qian, H.; Widenhoefer, R. A. *J. Am. Chem. Soc.* 2006, 128, 9066-9073. (f) Bender, C. F.; Widenhoefer, R. A. *Org. Lett.* 2006, 8, 5303-5305. (g) Bender, C. F.; Widenhoefer, R. A. *Chem. Commun.* 2006, 4143-4144. (h) Han, X.; Widenhoefer, R. A. *Angew. Chem., Int. Ed.* 2006, 45, 1747-1749.

(18) (xviii) (a) LaLonde, R. L.; Brenzovich, Jr., W. E.; Benitez, D.; Tkatchouk, E.; Kelley, K.; Goddard, III., W. A.; Toste, F. D. *Chem. Sci.*, 2010, 1, 226-233. (b) Roth, K. E.; Blum, S. A. *Organometallics* 2010, 29, 1712-1716.

(19) (xix) (a) Amijs, C. H. M.; López-Carrillo, V.; Raducan, M.; Pérez-Galán, P.; Ferrer, C.; Echavarren, A. M. *J. Org. Chem.* 2008, 73, 7721-7730. (b) Amijs, C. H. M.; Ferrer, C.; Echavarren, A. M. *Chem. Commun.* 2007, 698-700.

(20). (xx) In N,N,N'-trisubstituted ADCs, all atoms of the N—$C_{carbene}$—N unit have a flat, planar geometry. See ref 4.

Example 1

Supplemental Information

General:

All reactions were conducted in flame-dried glasswares under an inert atmosphere of dry argon. THF, $CH_2Cl_2$, $Et_2O$ and toluene were purified under positive pressure of dry nitrogen by Meyer Solvent Dispensing System prior to use. 1,4-Dioxane was dried over Na/benzophenone and was distilled. All the other chemicals used were purchased from Sigma-Aldrich Co., Acros Organics and Strem Chemicals Inc. and were used as received without further purification. NMR spectra were recorded using a Mercury-300 FT-NMR, operating at 300 MHz for $^1$H NMR and at 75.4 MHz for $^{13}$C NMR. All chemical shifts for $^1$H and $^{13}$C NMR spectroscopy were referenced to residual signals from CDCl$_3$ ($^1$H) 7.27 ppm, ($^{13}$C) 77.23 ppm and CD$_2$Cl$_2$ ($^1$H) 5.32 ppm, ($^{13}$C) 54.00 ppm. High resolution mass spectra were recorded on a Finnigan MAT95Q Hybrid Sector spectrometer or an Agilent 6210 TOF-LC/MS. The University of Florida Spectroscopic Services performed elemental analysis for compounds 5b.

Synthesis of ADC-Gold Complexes

N-(tert-Butyl)-N-phenylamine and N-(1-adamantyl)-N-phenylamine were synthesized by Pd-catalyzed coupling reactions.

N-(tert-butyl)-N-phenylamine (1a)

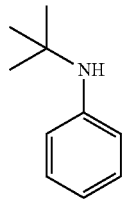

A mixture of Pd(dba)$_2$ (0.230 g, 0.400 mmol), (±)-2,2'-Bis(diphenylphosphino)-1,1'-binaphthalene (0.374 g, 0.601 mmol) and toluene (40 mL) in a sealed tube was stirred for 30 min at room temperature before adding tert-butylamine (1.80 mL, 17.1 mmol), bromobenzene (1.60 mL, 15.2 mmol) and sodium tert-butoxide (2.01 g, 20.9 mmol). The reaction solution was flushed with Ar for 1 min. and was stirred for 24 h at 100° C. After cooling the reaction mixture to room temperature, Et$_2$O (50 mL) was added. The reaction mixture was filtered through a pad of celite and was concentrated. Vacuum distillation of the crude mixture at 60° C. gave the desired product (1.876 g, 83.3%) as a colorless liquid. $^1$H NMR (300 MHz, CDCl$_3$) δ 7.17 (t, J=7.9 Hz, 2 H), 6.83-6.69 (m, 3H), 3.37 (br. s, 1H), 1.35 (s, 9H); $^{13}$C NMR (75 MHz, CDCl$_3$) δ 147.1, 129.1, 118.6, 117.7, 51.7, 30.3. HRMS-ESI (m/z): [M+H]$^+$ calcd for C$_{10}$H$_{15}$N, 150.1277. found, 150.1270.

N-(1-adamantyl)-N-phenylamine (1b)

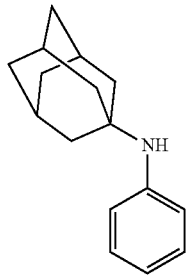 [SMILES: c1ccc(NC23CC4CC(CC(C4)C2)C3)cc1]

A mixture of Pd(dba)$_2$ (0.259 g, 0.450 mmol) and (±)-2,2'-Bis(diphenylphosphino)-1,1'-binaphthalene (0.417 g, 0.670 mmol) in toluene (40 mL) was stirred for 30 min at room temperature before adding 1-adamantylamine (2.269 g, 15.0 mmol), bromobenzene (1.60 mL, 15.2 mmol) and sodium tert-butoxide (2.02 g, 21.0 mmol). The reaction solution was stirred for 24 h at 100° C. After cooling the reaction mixture to room temperature, Et$_2$O (50 mL) was added. The reaction mixture was filtered through a pad of celite and was concentrated. Flash column chromatography (silicagel, 7:1 hexanes/EtOAc) afforded the desired product (2.239 g, 65.7%) as a pale yellow solid. $^1$H NMR (300 MHz, CDCl$_3$) δ 7.18 (t, J=7.6 Hz, 2H), 6.83 (m, 3H), 3.26 (br. s, 1H), 2.14 (m, 3H), 1.91 (m, 6H), 1.71 (m, 6H); $^{13}$C NMR (75 MHz, CDCl$_3$) δ 146.3, 129.0, 119.4, 119.3, 52.5, 43.8, 36.8, 30.0. HRMS-ESI (m/z): [M+H]$^+$ calcd for C$_{16}$H$_{21}$N, 228.1747. found, 228.1756.

N-(tert-butyl)-N-phenylformamide (2a)

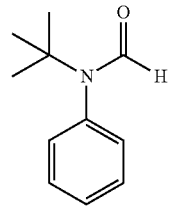

A solution of 1a (1.2212 g, 8.18 mmol) and acetic formic anhydride (1.2 mL, 15 mmol) in THF (10 mL) was stirred for 7 h at room temperature. To the reaction solution was added an aqueous NaOH solution (1.0 M, 20 mL) The organic phase was extracted with Et$_2$O (30 mL×2) and was chromatographed (4:1 hexanes/EtOAc) to give 2a (1:1 mixture of isomers, 1.076 g, 74.2%) as a white solid. $^1$H NMR (300 MHz, CDCl$_3$) δ 8.72 (s, 0.5H), 8.16 (s, 0.5H), 7.51-7.29 (m, 3H), 7.19-6.99 (m, 2H), 1.40 (s, 9H); $^{13}$C NMR (75 MHz, CDCl$_3$): δ 163.4, 162.6, 141.0, 138.2, 130.3, 130.1, 129.3, 129.2, 128.4, 57.7, 56.7, 31.0, 29.2. HRMS-ESI (m/z): [M+H]$^+$ calcd for C$_{11}$H$_{15}$NO, 178.1226. found: 178.1228.

N-(1-adamantyl)-N-phenylformamide (2b)

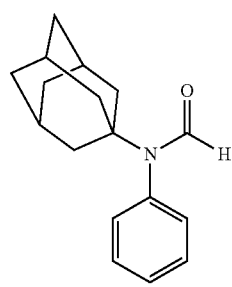 [SMILES: O=CN(c1ccccc1)C12CC3CC(CC(C3)C1)C2]

With the same method used in the synthesis of 2a, 2b (1:0.5 mixture of isomers, δ5.0%) was obtained as a white solid. $^1$H NMR (300 MHz, CDCl$_3$) δ 8.72 (s, 0.67H), 8.17 (s, 0.33H), 7.46-6.98 (m, 5H), 2.16-1.49 (m, 15H); $^{13}$C NMR (75 MHz, CDCl$_3$) δ 163.5, 162.2, 137.4, 130.8, 130.5, 129.1, 129.0, 128.4, 128.2, 58.9, 57.3, 43.6, 41.3, 36.5, 36.1, 30.2, 29.9. HRMS-ESI (m/z): [M+H]+ calcd for C$_{17}$H$_{21}$NO, 256.1696. found, 256.1697.

N-(tert-butyl)-N-(trimethylsilyl)benzeneamine (3a)

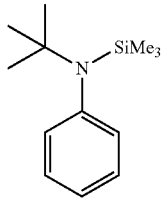

To a solution of 1a (0.972 g, 6.51 mmol) in THF (10 mL) was added nBuLi (1.6 M solution in hexanes) (4.3 mL, 6.9 mmol) at −78° C. After 30 min stirring of the reaction mixture at the same temperature, Me$_3$SiCl (0.89 mL, 7.0 mmol) was added at room temperature and the reaction mixture was stirred at 40° C. for 24 h. After evaporating all the volatiles by vacuum, pentane (50 mL) was added. After 20 min stirring of the mixture, stirring was stopped. The supernatant solution was transferred to another flask by a canula. Evaporation of the solvent gave 3a (1.016 g, 70.2%) as a pale yellow oil. $^1$H NMR (300 MHz, CDCl$_3$) 7.32-7.08 (m, 3H), 7.05-6.95 (m, 2H), 1.20 (s, 9H), 0.03 (s, 9H); $^{13}$C NMR (75 MHz, CDCl$_3$): δ 148.1, 133.6, 127.9, 124.9, 55.0, 32.1, 4.3. HRMS-ESI (m/z): [M+H]+ calcd for C$_{13}$H$_{23}$NSi, 222.1673. found, 222.1670.

N-(1-adamantyl)-N-(trimethylsilyl)benzeneamine (3b)

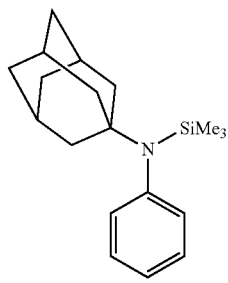 [SMILES: C[Si](C)(C)N(c1ccccc1)C12CC3CC(CC(C3)C1)C2]

With the same method used in the synthesis of 3a, a mixture of 3b (47.2%) and the reactant 3a (37.0%) was obtained. The ratio (product:reactant, 56:44) was calculated by $^1$H NMR. They were inseparable and used in the synthesis of 4b without further purification. $^1$H NMR (300 MHz, CDCl$_3$) δ 7.22-7.14 (m, 3H), 7.02-6.99 (m, 2H), 2.04 (br s, 3H), 1.80 (br s, 6H), 1.59 (br s, 6H), 0.05 (s, 9H); $^{13}$C NMR (75 MHz, CDCl$_3$) δ 146.6, 134.0, 127.8, 124.9, 55.5, 44.9, 36.8, 30.4, 4.7. HRMS-DIP-CI (m/z): [M]+ calcd for C$_{19}$H$_{29}$NSi, 299.2069. found, 299.2072.

N,N'-Bis(tert-butyl)-N,N'-diphenylformamidinium chloride (4a)

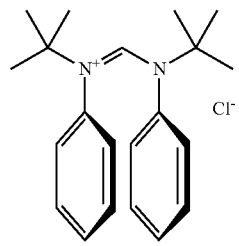

Oxalyl chloride (0.42 mL, 5.0 mmol) was added dropwise to a solution of 2a (0.582 g, 3.28 mmol) in toluene (10 mL) at −78° C. The reaction mixture was stirred for 2 h at room temperature. After evaporation of all the volatiles by vacuum, CH$_2$Cl$_2$ (10 mL) was added. 3a (0.778 g, 3.50 mmol) was added to the reaction solution at −78° C., and the reaction mixture was slowly warmed to room temperature for 30 min. After stirring for 3 h at room temperature, the reaction solution was concentrated to 2 mL. The solution was dropped to a rapidly stirred hexanes (10 mL). The precipitated solid was collected and was washed with hexane (10 mL×2) to give 4a (1.028 g, 90.8%) as a white solid. $^1$H NMR (300 MHz, CDCl$_3$) δ 8.90 (s, 1H), 7.11-6.78 (m, 10H), 1.56 (s, 18H); $^{13}$C NMR (75 MHz, CDCl$_3$) δ 153.8, 136.1, 130.3, 128.9, 66.2, 29.7. HRMS-ESI (m/z): [M]+ calcd for C$_{21}$H$_{29}$ClN$_2$, 309.2325. found, 309.2322.

N,N'-Bis(1-adamantyl)-N,N'-diphenylformamidinium chloride (4b)

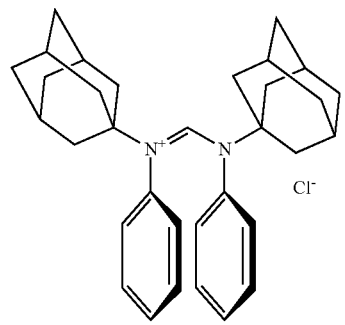

With the same method used in the synthesis of 4a except for adding 3b (2 equiv), 4b (71.5%) was obtained as a white solid. $^1$H NMR (300 MHz, CD$_2$Cl$_2$) δ=8.71 (s, 1H), 7.24-6.90 (m, 6H), 6.78 (d, J=7.4 Hz, 4H), 2.21 (br. s, 6H), 2.07-1.99 (m, 12H), 1.66 (br. s, 12H); $^{13}$C NMR (75 MHz, CD$_2$Cl$_2$) δ 152.7, 135.0, 130.3, 129.0, 128.9, 66.6, 41.8, 35.4, 30.5. HRMS-DART (m/z): [M]+ calcd for C$_{33}$H$_{41}$ClN$_2$, 465.3264. found, 465.3249.

[N,N'-Bis(tert-butyl)-N,N'-diphenyldiaminocarbene]gold(I) chloride (5a)

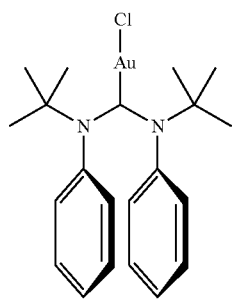

To a suspension of 4a (69.0 mg, 0.200 mmol) in THF (2 mL) was added LiHMDS (1.0 M solution in THF) (0.21 mL, 0.21 mmol) at −78° C. After 30 min stirring, Me$_2$S.AuCl (59.2 mg, 0.201 mmol) was added at −78° C. The reaction mixture was slowly warmed to room temperature and was stirred for 1.5 h. The reaction solution was loaded on the column of flash silica and was chromatographed (4:1 hexanes/EtOAc) to give 5a (84.5 mg, 78.0%) as an off-white solid. $^1$H NMR (300 MHz, CDCl$_3$) δ 7.18-7.08 (m, 2H), 7.06-6.94 (m, 4 H), 6.23 (d, J=7.36 Hz, 4H), 1.69 (s, 18H); $^{13}$C NMR (75 MHz, CDCl$_3$): δ 216.5, 144.7, 130.2, 128.5, 127.1, 63.0, 32.3. HRMS-ESI (m/z): [M+Na]$^+$ calcd for C$_{21}$H$_{29}$AuClN$_2$, 563.1499. found, 563.1516.

[N,N'-Bis(1-adamantyl)-N,N'-diphenyldiaminocarbene]gold(I) chloride (5b)

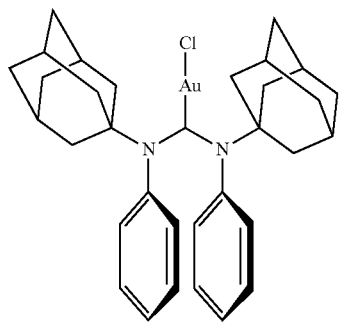

With the same method used in the synthesis of 5a, 5b (49.6%) was obtained as an off-white solid. $^1$H NMR (300 MHz, CDCl$_3$) δ 7.16-7.07 (m, 2H), 7.04-6.91 (m, 4H), 6.19 (d, J=7.6 Hz, 4H), 2.46 (br. s, 12H), 2.11 (br. s, 6H), 1.69-1.54 (m, 12H); $^{13}$C NMR (75 MHz, CDCl$_3$) δ 215.8, 143.7, 130.6, 128.2, 126.9, 64.0, 43.7, 36.0, 30.7. Anal. calcd for C$_{33}$H$_{40}$AuClN$_2$: C, 56.78; H, 5.92; N, 4.01. found: C, 56.44; H, 5.90; N, 3.87.

[Bis(pyrrolidyl)diaminocarbene]gold(I) chloride (5c)

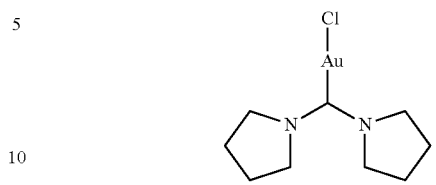

1-(Chloro-1-pyrrolidinylmethylene)pyrrolidinium tetrafluoroborate (77.5 mg, 0.282 mmol) in THF (2 mL) was treated with nBuLi (1.6 M solution in hexanes) (0.190 mL, 0.310 mmol) at −78° C. After 15 min, Me$_2$S.AuCl (83.1 mg, 0.282 mmol) was added at −78° C. The reaction mixture was slowly warmed to room temperature and was stirred for 2 h before being loaded on the column of flash silica for chromatography (1:1 hexanes/EtOAc) to give 5c (38.5 mg, 35.5%). $^1$H NMR (300 MHz, CDCl$_3$) δ 3.78 (br. s, 8H), 2.02-1.72 (m, 8H); $^{13}$C NMR (75 MHz, CDCl$_3$) δ 194.4, 54.8, 25.5; HRMS-DIP-CI (m/z): [M]$^+$ calcd for C$_9$H$_{16}$AuClN$_2$, 384.0668. found, 384.0687.

Gold(I)-Catalyzed Organic Reactions

Catalysts 5d[5], 5e[6], 5f[7] and 5g[8] were synthesized by the published methods.

Intramolecular hydroamination (Table 2):

A mixture of gold-chloride catalyst (5.0 mmol) and AgOTf (5.0 μmol) in 1,4-dioxane was stirred for 30 min before adding N-(2,2-Diphenyl-4-pentenyl)-N'-phenylurea (7)[9](0.100 mmol). After stirring the reaction mixture for a specified time at room temperature, an aliquot (1 mL) of the reaction solution was taken and filtered. After evaporation of the solvent in vacuo, the conversion was calculated by $^1$H NMR comparing the integration of the reactant (7) and the product (8).

Indole addition to 1,6-enyne (Table 3):

A mixture of gold-chloride catalyst (7.5 μmol) and AgSbF$_6$ (7.5 μmol) was stirred for 15 min before adding 9[10] (0.150 mmol) and indole (0.165 mmol) at room temperature. The mixture was stirred for a specified time at room temperature and purified by column chromatography (silicagel, 5:1 hexanes/EtOAc). The product ratio between 10 and 11 was calculated by $^1$H NMR comparing the integration of the two products. FIGS. 3.1A to 3.1V illustrates $^1$H NMR of compound 1a, 1b, 2a, 2b, 3a, 3b, 4a, 4b, 5a, 5b, and 5c.

5a (CCDC-781470)

Data were collected at 100 K on a Bruker DUO system equipped with an APEX II area detector and a graphite monochromator utilizing MoK$_\alpha$ radiation (λ=0.71073 Å). Cell parameters were refined using up to 9999 reflections. A hemisphere of data was collected using the co-scan method (0.5° frame width). Absorption corrections by integration were applied based on measured indexed crystal faces. The structure was solved by the Direct Methods in SHELXTL6, and refined using full-matrix least squares.

The non-H atoms were treated anisotropically, whereas the hydrogen atoms were calculated in ideal positions and were riding on their respective carbon atoms. A total of 226 parameters were refined in the final cycle of refinement using 4647 reflections with I>2σ(I) to yield R$_1$, and wR$_2$ of 1.88% and 5.03%, respectively. Refinement was done using $F^2$. The structure of compound 5a is shown in FIG. 3.2.

| | |
|---|---|
| Empirical formula | $C_{21}H_{28}AuClN_2$ |
| Formula weight | 540.87 |
| Temperature | 100(2) K |
| Wavelength | 0.71073 Å |
| Crystal system | Monoclinic |
| Space group | $P2_1/n$ |
| Unit cell dimensions | a = 14.8970(11) Å    α = 90°. |
| | b = 9.1140(6) Å    β = 109.832(1)°. |
| | c = 16.3705(12) Å    γ = 90°. |
| Volume | 2090.8(3) Å$^3$ |
| Z | 4 |
| Density (calculated) | 1.718 Mg/m$^3$ |
| Absorption coefficient | 7.170 mm$^{-1}$ |
| F(000) | 1056 |
| Crystal size | 0.30 × 0.25 × 0.15 mm$^3$ |
| θ range for data collection | 2.27 to 27.50°. |
| Index ranges | −19 ≤ h ≤ 18, −11 ≤ k ≤ 10, −21 ≤ l ≤ 19 |
| Reflections collected | 27404 |
| Independent reflections | 4809 [$R_{int}$ = 0.0763] |
| Completeness to θ = 27.50° | 100.0% |
| Absorption correction | Numerical |
| Max. and min. transmission | 0.4208 and 0.2238 |
| Refinement method | Full-matrix least-squares on $F^2$ |
| Data/restraints/parameters | 4809/0/226 |
| Goodness-of-fit on $F^2$ | 1.108 |
| Final R indices [I > 2σ(I)] | $R_1$ = 0.0188, $wR_2$ = 0.0503 [4647] |
| R indices (all data) | $R_1$ = 0.0195, $wR_2$ = 0.0506 |
| Largest diff. peak and hole | 1.326 and −1.378 e·Å$^{-3}$ |

5b (CCDC-781471)

Data were collected at 173 K on a Siemens SMART PLATFORM equipped with A CCD area detector and a graphite monochromator utilizing MoK$_\alpha$ radiation (λ=0.71073 Å). Cell parameters were refined using up to 8192 reflections. A full sphere of data (1850 frames) was collected using the ω-scan method (0.3° frame width). The first 50 frames were re-measured at the end of data collection to monitor instrument and crystal stability (maximum correction on I was <1%). Absorption corrections by integration were applied based on measured indexed crystal faces. The structure of compound 5b is shown in FIG. 3.3.

The structure was solved by the Direct Methods in SHELXTL6, and refined using full-matrix least squares. The non-H atoms were treated anisotropically, whereas the hydrogen atoms were calculated in ideal positions and were riding on their respective carbon atoms. The complex is located on a 2-fold rotation axis thus half is contained in the asymmetric unit. A total of 169 parameters were refined in the final cycle of refinement using 2994 reflections with I>2σ(I) to yield $R_1$ and $wR_2$ of 1.13% and 2.82%, respectively. Refinement was done using $F^2$.

| | |
|---|---|
| Empirical formula | $C_{33}H_{40}AuClN_2$ |
| Formula weight | 697.09 |
| Temperature | 100(2) K |
| Wavelength | 0.71073 Å |
| Crystal system | Tetragonal |
| Space group | $P4_32_12$ |
| Unit cell dimensions | a = 10.5907(4) Å    α = 90°. |
| | b = 10.5907(4) Å    β = 90°. |
| | c = 23.7251(10) Å    γ = 90°. |
| Volume | 2661.08(18) Å$^3$ |
| Z | 4 |
| Density (calculated) | 1.740 Mg/m$^3$ |
| Absorption coefficient | 5.655 mm$^{-1}$ |
| F(000) | 1392 |
| Crystal size | 0.22 × 0.10 × 0.05 mm$^3$ |
| θ range for data collection | 2.11 to 27.50°. |
| Index ranges | −13 ≤ h ≤ 13, −13 ≤ k ≤ 13, −30 ≤ l ≤ 30 |
| Reflections collected | 33575 |
| Independent reflections | 3066 [$R_{int}$ = 0.0293] |
| Completeness to θ = 27.50° | 100.0% |
| Absorption correction | Numerical |
| Max. and min. transmission | 0.7770 and 0.3706 |
| Refinement method | Full-matrix least-squares on $F^2$ |
| Data/restraints/parameters | 3066/0/169 |
| Goodness-of-fit on $F^2$ | 1.142 |
| Final R indices [I > 2σ(I)] | $R_1$ = 0.0112, $wR_2$ = 0.0282 [2994] |
| R indices (all data) | $R_1$ = 0.0118, $wR_2$ = 0.0283 |
| Absolute structure parameter | 0.001(5) |
| Largest diff. peak and hole | 0.566 and −0.389 e·A$^{-3}$ |

5c (CCDC-781472)

Data were collected at 173 K on a Siemens SMART PLATFORM equipped with A CCD area detector and a graphite monochromator utilizing MoK$_\alpha$ radiation (λ=0.71073 Å). Cell parameters were refined using up to 8192 reflections. A full sphere of data (1850 frames) was collected using the ω-scan method (0.3° frame width). The first 50 frames were re-measured at the end of data collection to monitor instrument and crystal stability (maximum correction on I was <1%). Absorption corrections by integration were applied based on measured indexed crystal faces. The structure of 5c is shown in FIG. 3.4.

The structure was solved by the Direct Methods in SHELXTL6, and refined using full-matrix least squares. The non-H atoms were treated anisotropically, whereas the hydrogen atoms were calculated in ideal positions and were riding on their respective carbon atoms. A total of 118 parameters were refined in the final cycle of refinement using 2397 reflections with I>2σ(I) to yield $R_1$ and $wR_2$ of 1.46% and 3.63%, respectively. Refinement was done using $F^2$.

| | |
|---|---|
| Empirical formula | $C_9H_6AuClN_2$ |
| Formula weight | 384.65 |
| Temperature | 173(2) K |
| Wavelength | 0.71073 Å |
| Crystal system | Monoclinic |
| Space group | $P2_1/n$ |
| Unit cell dimensions | a = 9.2980(6) Å    α = 90°. |
| | b = 9.6606(6) Å    β = 99.610(1)°. |
| | c = 12.1098(7) Å    γ = 90°. |
| Volume | 1072.49(11) Å$^3$ |
| Z | 4 |
| Density (calculated) | 2.382 Mg/m$^3$ |
| Absorption coefficient | 13.923 mm$^{-1}$ |
| F(000) | 720 |
| Crystal size | 0.17 × 0.09 × 0.02 mm$^3$ |
| θ range for data collection | 2.57 to 27.49°. |
| Index ranges | −12 ≤ h ≤ 12, −9 ≤ k ≤ 12, −15 ≤ l ≤ 15 |
| Reflections collected | 7516 |
| Independent reflections | 2464 [$R_{int}$ = 0.0278] |
| Completeness to θ = 27.49° | 100.0% |
| Absorption correction | None |
| Max. and min. transmission | 0.7682 and 0.1956 |
| Refinement method | Full-matrix least-squares on $F_2$ |
| Data/restraints/parameters | 2464/0/118 |
| Goodness-of-fit on $F^2$ | 1.082 |
| Final R indices [I > 2σ(I)] | $R_1$ = 0.0146, $wR_2$ = 0.0363 [2397] |
| R indices (all data) | $R_1$ = 0.0150, $wR_2$ = 0.0365 |
| Largest diff. peak and hole | 0.853 and −1.231 e·Å$^{-3}$ |

% $V_{Bur}$ of Gold Complexes

% $V_{Bur}$s were calculated using SamVca. program which is available on the web: www.molnac.unisa.it/Omtools/sambvca.php. The input files were made with Chem3D Cartesian format by removing other atoms except for the carbene parts from the X-ray structures (5a: CCDC-781470, 5b: CCDC-781471, 5c: CCDC-781472, 5d[8]: CCDC-766153, 5e[8]: CCDC-766158, 5f[6]: CCDC-247531, 5g[7]: CCDC-258274).

Example 2

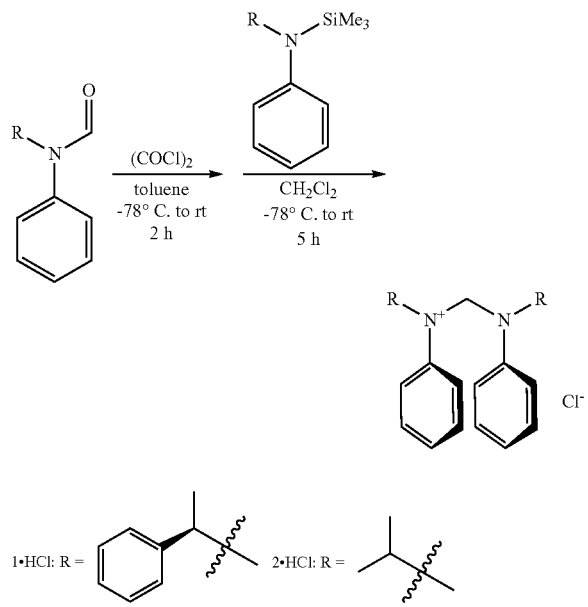

Synthesis of 1.HCl

To a stirred solution of (S)—N-phenyl-N-(1-phenylethyl)formamide (0.4404 g, 1.95 mmol) in toluene (10 mL) was dropped oxalyl chloride (0.25 mL, 3.0 mmol) at −78° C., and the reaction mixture was stirred for 2 h at room temperature. After evaporation of all the volatiles, $CH_2Cl_2$ (5 mL) was charged in the reaction flask.

N-(trimethylsilyl)-N-(1-phenylethyl)aniline (0.54 mL, 2.0 mmol) was added in the reaction solution at −78° C. and the reaction mixture was stirred for 5 h at room temperature. The solution was concentrated to 1.0 mL, and the product was recrystallized and washed with hexanes (10 mL×2). Yield: 0.7756 g, 1.76 mmol, 90.3%. $^1$H NMR (300 MHz, $CDCl_3$) δ 11.03 (s, 1H), 7.41-7.21 (m, 10H), 6.95-6.82 (m, 4H), 6.70-6.58 (m, 4H), 6.27 (q, J=7.1 Hz, 2H), 5.78 (d, J=7.8 Hz, 2H), 1.59 (d, J=6.8 Hz, 6H); $^{13}$C NMR 157.3, 137.7, 134.1, 129.6, 129.4, 129.1, 129.0, 128.8, 128.7, 128.6, 128.5, 66.7, 18.2. HRMS-ESI (m/z): [M]$^+$ calcd for $C_{29}H_{29}N_2$, 405.2325. found, 405.2344.

Synthesis of 2.HCl

2.HCl (1.24 g, 64%) was obtained from N-isopropyl-N-phenylformamide (1.00 g, 6.13 mmol). $^1$H NMR (500 MHz, $CDCl_3$) δ 10.52 (s, 1H), 7.10-7.05 (m, 2H), 7.04-6.99 (m, 4H), 6.73-6.69 (m, 4H), 5.12 (quin, J=6.6 Hz, 2H), 1.25 (d, J=6.6 Hz, 12H); $^{13}$C NMR (126 MHz, $CDCl_3$) δ 157.2, 134.1, 129.5, 129.1, 129.1, 61.0, 21.9. HRMS-ESI (m/z): [M]$^+$ calcd for $C_{19}H_{25}N_2$, 281.20. found, 281.2020.

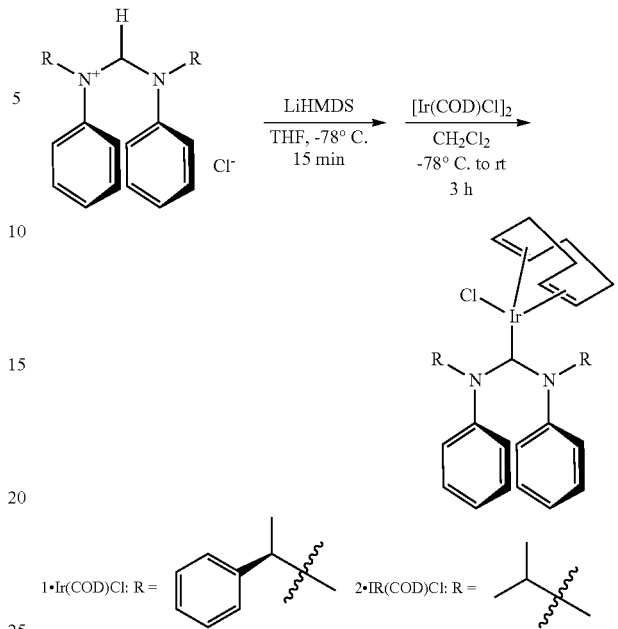

Synthesis of 1.Ir(COD)Cl Complex

To a stirred solution of amidinium 1.HCl (47.2 mg, 0.107 mmol) was dropped a 1.0 M solution of LiHMDS in THF (0.11 mL, 0.11 mmol) at −78° C. After 15 min at −78° C., [Ir(COD)Cl]$_2$ (33.6 mg, 0.0500 mmol) was added in the reaction solution, and the temperature was increased to room temperature. Stirring for 3 h at room temperature completed the reaction. The reaction solution was loaded on a silicagel column and eluted with a mixed solvent (hexanes:ethyl acetate, 7:1). Yield: 51.2 mg, 64.7%. $^1$H NMR (300 MHz, $CDCl_3$) δ 7.85 (d, J=7.6 Hz, 2H), 7.78-7.58 (m, 2H), 7.42-7.20 (m, 9H), 7.08 (t, J=7.2 Hz, 1H), 6.96-6.65 (m, 4H), 6.37-6.17 (m, 2H), 5.12 (d, J=7.4 Hz, 1H), 4.87 (d, J=8.5 Hz, 1H), 4.82-4.63 (m, 2H), 3.70 (br s, 2H), 2.40 (br s, 1H), 2.30-2.10 (m, 2H), 2.08-1.60 (m, 4H), 1.59-1.38 (m, 7H)

Synthesis of 2.Ir(COD)Cl Complex

2.Ir(COD)Cl (0.110 g, 62%) was obtained from 2.HCl (75.0 mg, 0.24 mmol). $^1$H NMR (500 MHz, $CDCl_3$) δ 7.05-6.83 (m, 6H), 6.73-6.54 (m, 4H), 6.22 (d, J=7.7 Hz, 2H), 4.67-4.55 (m, 2H), 3.38-3.25 (m, 2H), 2.36-2.21 (m, 4H), 1.85-1.75 (m, 2H), 1.75-1.64 (m, 2H), 1.19 (d, J=6.7 Hz, 6H), 1.09 (d, J=6.7 Hz, 6H). $^{13}$C NMR (75 MHz, $CDCl_3$, δ): 143.9, 129.8, 129.2, 128.6, 128.3, 126.0, 82.6, 59.5, 52.3, 33.5, 29.6, 22.5, 22.2.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional

We claim at least the following:

1. A compound, comprising a formula of compound A:

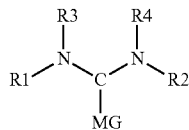

wherein R1 and R2 are independently selected from a secondary alkyl group, unsubstituted or substituted, or a tertiary alkyl group, unsubstituted or substituted, R3 and R4 are independently selected from an aryl group, and MG is a metal group.

2. The compound of claim 1, wherein the metal of the metal group includes a metal selected from the group consisting of: Au, Pt, Ir, Rh, Re, Ru, Ni, Pd, Cu, Fe, and Co.

3. The compound of claim 2, wherein MG is AuCl and R3 and R4 are each a phenyl group.

4. The compound of claim 3, wherein the R1 and R2 are each a tert-butyl group.

5. The compound of claim 3, wherein the R1 and R2 are each an adamantyl group.

6. The compound of claim 1, wherein R3 and R4 are each a phenyl group.

7. The compound of claim 1, wherein the R1 and R2 are each a tert-butyl group.

8. The compound of claim 1, wherein the R1 and R2 are each an adamantyl group.

9. The compound of claim 1, wherein the metal of the metal group includes a metal selected from the group consisting of: Au, Pt, Ir, Rh, Re, Ru, Ni, Pd, Cu, Fe, and Co, and the metal group includes one or more groups bonded to the metal, wherein the group is selected from the group consisting of: Cl, Br, I, $BF_4$, $PF_6$, $BAr_4$, $ClO_4$, OAc, OTf, Ts, Ms, $NTf_2$, and $PO_2Cl_2$.

10. A compound, comprising a formula of compound A:

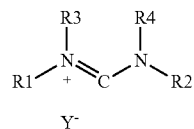

wherein R1 and R2 are independently selected from a secondary alkyl group, unsubstituted or substituted, or a tertiary alkyl group, unsubstituted or substituted, R3 and R4 are independently an aryl group, Y is selected from the group consisting of: Cl, Br, I, $BF_4$, $PF_6$, $BAr_4$, $ClO_4$, OAc, OTf, Ts, Ms, $NTf_2$, and $PO_2Cl_2$.

11. The compound of claim 10, wherein R3 and R4 are each a phenyl group.

12. The compound of claim 10, wherein the R1 and R2 are each a tert-butyl group.

13. The compound of claim 10, wherein the R1 and R2 are each an adamantyl group.

14. The compound of claim 10, wherein R3 and R4 are each a phenyl group and R1 and R2 are each a tert-butyl group.

15. The compound of claim 10, wherein R3 and R4 are each a phenyl group and R1 and R2 are each an adamantyl group.

* * * * *